US012741959B2

(12) United States Patent
Schueller et al.

(10) Patent No.: US 12,741,959 B2
(45) Date of Patent: Sep. 22, 2026

(54) BELUMOSUDIL METABOLITES AND USES THEREOF IN THE TREATMENT OF CHRONIC GRAFT-VERSUS-HOST DISEASE

(71) Applicant: Kadmon Corporation, LLC, Bridgewater, NJ (US)

(72) Inventors: Olivier Schueller, Cambridge, MA (US); Jeegar P. Patel, Hillsborough, NJ (US)

(73) Assignee: Kadmon Corporation, LLC, Morristown, NJ (US)

( * ) Notice: Subject to any disclaimer, the term of this patent is extended or adjusted under 35 U.S.C. 154(b) by 0 days.

(21) Appl. No.: 18/595,801

(22) Filed: Mar. 5, 2024

(65) Prior Publication Data

US 2024/0262810 A1 Aug. 8, 2024

Related U.S. Application Data

(60) Division of application No. 18/105,427, filed on Feb. 3, 2023, now Pat. No. 11,952,369, which is a continuation of application No. PCT/US2022/037210, filed on Jul. 14, 2022.

(51) Int. Cl.
*C07D 403/12* (2006.01)
*A61K 47/54* (2017.01)

(52) U.S. Cl.
CPC .......... *C07D 403/12* (2013.01); *A61K 47/549* (2017.08)

(58) Field of Classification Search
CPC .................................................... C07D 403/12
See application file for complete search history.

(56) References Cited

U.S. PATENT DOCUMENTS

| | | | |
|---|---|---|---|
| 6,218,410 | B1 | 4/2001 | Uehata et al. |
| 6,924,292 | B2 | 8/2005 | Kawano et al. |
| 8,357,693 | B2 | 1/2013 | Bartolozzi et al. |
| 8,916,576 | B2 | 12/2014 | Bartolozzi et al. |
| 9,815,820 | B2 | 11/2017 | Poyurovsky et al. |
| 10,183,931 | B2 | 1/2019 | Poyurovsky et al. |
| 10,696,660 | B2 | 6/2020 | Poyurovsky et al. |
| 11,311,541 | B2 | 4/2022 | Zanin-Zhorov et al. |
| 11,952,369 | B2 | 4/2024 | Schueller et al. |
| 12,097,202 | B2 | 9/2024 | Eiznhamer et al. |
| 2003/0087919 | A1 | 5/2003 | Nagarathnam et al. |
| 2003/0125344 | A1 | 7/2003 | Nagarathnam et al. |
| 2003/0220357 | A1 | 11/2003 | Bankston et al. |
| 2004/0002508 | A1 | 1/2004 | Nagarathnam et al. |
| 2005/0014783 | A1 | 1/2005 | Dole et al. |
| 2006/0009460 | A1 | 1/2006 | Dickson et al. |
| 2009/0203690 | A1 | 8/2009 | Akritopoulou-Zanze et al. |
| 2009/0306086 | A1 | 12/2009 | Ibrahim et al. |
| 2010/0093719 | A1 | 4/2010 | Campbell et al. |
| 2010/0144707 | A1 | 6/2010 | Bartolozzi et al. |
| 2010/0324037 | A1 | 12/2010 | Campbell et al. |
| 2011/0172422 | A1 | 7/2011 | Campbell et al. |
| 2012/0202793 | A1 | 8/2012 | Sweetnam et al. |
| 2012/0283229 | A1 | 11/2012 | Glick |
| 2013/0131047 | A1 | 5/2013 | Bartolozzi et al. |
| 2015/0238601 | A1 | 8/2015 | Boxer et al. |
| 2015/0252025 | A1 | 9/2015 | Poyurovsky et al. |
| 2017/0000884 | A1 | 1/2017 | Betts et al. |
| 2017/0112832 | A1 | 4/2017 | Zanin-Zhorov et al. |
| 2019/0328721 | A1 | 10/2019 | Nam et al. |
| 2021/0147391 | A1 | 5/2021 | Poyurovsky et al. |
| 2022/0160709 | A1 | 5/2022 | Mehta et al. |
| 2023/0381179 | A1 | 11/2023 | Aggarwal et al. |
| 2024/0024322 | A1 | 1/2024 | Schueller et al. |
| 2024/0024323 | A1 | 1/2024 | Patel |

FOREIGN PATENT DOCUMENTS

| | | | |
|---|---|---|---|
| RU | 2206321 | C2 | 6/2003 |
| RU | 2003103606 | A | 8/2004 |
| RU | 2003104284 | A | 8/2004 |
| TW | 202412807 | A | 4/2024 |
| TW | 202425996 | A | 7/2024 |
| WO | 2002048676 | A2 | 6/2002 |
| WO | 2002076976 | A2 | 10/2002 |
| WO | 2003012392 | A2 | 2/2003 |
| WO | 2003018854 | A2 | 3/2003 |
| WO | 2003054515 | A2 | 7/2003 |
| WO | 2005120509 | A1 | 12/2005 |
| WO | 2006105081 | A2 | 10/2006 |
| WO | 2008054599 | A2 | 5/2008 |
| WO | 2009152083 | A1 | 12/2009 |
| WO | 2011062766 | A2 | 5/2011 |
| WO | 2011107608 | A1 | 9/2011 |
| WO | 2012006202 | A1 | 1/2012 |
| WO | 2012040499 | A2 | 3/2012 |
| WO | 2012067965 | A1 | 5/2012 |
| WO | 2012135697 | A2 | 10/2012 |

(Continued)

OTHER PUBLICATIONS

Anonymous: "Application No. 214783Orig1s000: Multi-Discipline Review Summary Review Clinical Review Non-Clinical Review Statistical Review Clinical Pharmacology Review", Jul. 16, 2021, retrieved from the internet: https://www.accessdata.fda.gov/drugsatfda_docs/nda/2021/214783Orig1s000MultidisciplineR.pdf [retrieved on Feb. 20, 2023], 325 pages.
Anonymous: "Belumosudil Pregnancy and Breastfeeding Warnings", Jun. 21, 2022, retrieved from the internet: https://www.drugs.com/pregnancy/belumosudil.html on Feb. 17, 2023, 2 pages.
Anonymous: Highlights of Prescribing Information: Rezurock (TM) (belumosudil) tablets, for oral use Initial U.S. Appoval: 2021, retrieved from the internet: https://www.rezurockhcp.com/full-prescribing-information.pdf [retrieved on Feb. 20, 2023], 16 pages.
Bachier, Carlos R. et al., "Epidemiology and Real-World Treatment of Chronic Graft-Versus-Host Disease Post Allogeneic Hematopoietic Cell Transplantation: A US Claims Analysis", Blood (2019) 134 (Supplement_1): 2109.

(Continued)

*Primary Examiner* — Brian E McDowell
(74) *Attorney, Agent, or Firm* — McNeill PLLC

(57) ABSTRACT

The present disclosure provides metabolites of belumosudil and uses of the metabolites in of treating patients with ROCK2-mediated diseases including cGVHD.

2 Claims, 3 Drawing Sheets

(56) References Cited

FOREIGN PATENT DOCUMENTS

| | | | |
|---|---|---|---|
| WO | 2012146724 | A2 | 11/2012 |
| WO | 2013030216 | A1 | 3/2013 |
| WO | 2013030365 | A1 | 3/2013 |
| WO | 2013030366 | A1 | 3/2013 |
| WO | 2013030367 | A1 | 3/2013 |
| WO | 2014055996 | A2 | 4/2014 |
| WO | 2015127310 | A1 | 8/2015 |
| WO | 2015157556 | A1 | 10/2015 |
| WO | 2021011873 | A1 | 1/2021 |
| WO | 2021030619 | A1 | 2/2021 |
| WO | 2021096951 | A1 | 5/2021 |
| WO | 2021129589 | A1 | 7/2021 |
| WO | 2022020850 | A1 | 1/2022 |
| WO | 2022170864 | A1 | 8/2022 |
| WO | 2023205153 | A1 | 10/2023 |
| WO | 2024015065 | A1 | 1/2024 |
| WO | 2024015066 | A1 | 1/2024 |
| WO | 2024015067 | A1 | 1/2024 |
| WO | 2024015068 | A1 | 1/2024 |
| WO | 2024064757 | A1 | 3/2024 |
| WO | 2024118556 | A1 | 6/2024 |
| WO | 2024124084 | A1 | 6/2024 |
| WO | 2025019544 | A1 | 1/2025 |

OTHER PUBLICATIONS

Carpenter, Paul A. et al., "A phase II/III randomized, multicenter trial of prednisone/sirolimus versus prednisone/sirolimus/calcineurin inhibitor for the treatment of chronic graft-versus-host disease: BMT CTN 0801," Haematologica 2018, 103(11): 1915-1924.
Chen, Jiezhong et al., "Roles of rifampicin in drug-drug interations: underlying molecular mechanisms involving the nuclear pregnane X receptor", Ann Clin Microbiol Antimicrob, 2006, 5:3, 11 pages.
Hardin, Thomas C. et al., "Pharmacokinetics of Itraconazole following Oral Administration to Normal Volunteers", Antimicrobial Agents and Chemotherapy, Sep. 1988, 32(9), 1310-1313.
Kantola, Teemu et al., "Effect of itraconazole on the pharmacokinetics of atorvastatin", Clinical Pharmacology & Therapeutics, 64 (1), 1998, 58-65.
Lebrun-Vignes, B. et al., "Effect of itraconazole on the pharmacokinetics of prednisolone and methylprednisolone and cortisol secretion in healthy subjects", Br J Clin Pharmacol, 51, 2001, 443-450.
Lee, Stephanie J. et al., "Development and Validation of a Scale to Measure Symptoms of Chronic Graft-versus-Host Disease", Biology of Blood and Marrow Transplantation 8:444-452 (2002).
Lee, Stephanie J. et al., "Success of Immunosuppressive Treatments in Patients with Chronic Graft-versus-Host Disease", Biol Blood Marrow Transplant 24 (2018) 555-562.
Martin, Paul J. et al., "An endpoint associated with clinical benefit after initial treatment of chronic graft-versus-host disease", Blood, 2017, 130:3, 360-367.
PCT International Search Report and Written Opinion for PCT/US2022/037207, mailed on Mar. 2, 2023, 10 pages.
PCT International Search Report and Written Opinion from PCT/US2022/037200, mailed Mar. 2, 2023, 10 pages.
PCT International Search Report from PCT/US2022/037192, mailed on Mar. 2, 2023, 10 pages.
PCT International Search Report from PCT/US2022/037210, mailed on Mar. 2, 2023, 10 pages.
Przepiorka, Donna et al., "FDA Approval Summary: Belumosudil for Adult and Pediatric Patients 12 Years and Older with Chronic GVHD After Two or More Prior Lines of Systemic Therapy", Clin Cancer Res. Jun. 1., 2022; 28 (12): 2488-2492.
Schueller, Olivier et al., "A Phase I Pharmacokinetic Drug Interaction Study of Belumosudil Coadministered With CYP3A4 Inhibitors and Inducers and Proton Pump Inhibitors", Clinical Pharmacology In Drug Development, vol. 11, No. 7, Mar. 1, 2022, pp. 795-806.
Schueller, Olivier et al., "Absolute Bioavailability, Mass Balance, and Metabolic Profiling Assessment of [I4C]Belumosudil in Healthy Men: A Phase I, Open-Label, 2-Part Study", Clinical Pharmacology in Drug Development, 2022, 11(7) 786-794.
Schueller, Olivier et al., "Phase I Studies to Evaluate the Food Effect and Relative Bioavailability of Tablet and Capsule Formulations of Belumosudil in Healthy Adult Subjects", Clinical Pharmacology in Drug Development, vol. 11, No. 7, Mar. 2, 2022, pp. 807-814.
Waller, Edmund K. et al., "Ibrutinib for Chronic Graft-versus-Host Disease After Failure of Prior Therapy: 1-Year Update of a Phase 1b/2 Study", Biol Blood Marrow Transplant 25 (2019) 2002-2007.
Baharlou, Simin, PCT International Preliminary Report on Patentability and Written Opinion from PCT/US2023/081268, mailed Jun. 12, 2025, 13 pages.
Baharlou, Simin, PCT International Preliminary Report on Patentability and Written Opinion from PCT/US2023/083039, mailed Jun. 19, 2025, 8 pages.
Beyss-Kahana, Ellen, Extended European Search Report from EP22175888.1, mailed Feb. 23, 2023, 11 pages.
Beyss-Kahana, Ellen, Supplementary European Search Report from EP13843426.1 mailed Apr. 11, 2017, 13 pages.
Fritz, Martin, Supplementary European Search Report from EP06748799.1, mailed Dec. 22, 2011, 6 pages.
John, Tatjana, PCT International Search Report and Written Opinion from PCT/US2024/038315, mailed Oct. 25, 2024, 14 pages.
Lee, Sun Hwa, PCT International Preliminary Report on Patentability and Written Opinion from PCT/US2022/037192, mailed Jan. 23, 2025, 8 pages.
Lee, Sun Hwa, PCT International Preliminary Report on Patentability and Written Opinion from PCT/US2022/037200, mailed Jan. 23, 2025, 8 pages.
Lee, Sun Hwa, PCT International Preliminary Report on Patentability and Written Opinion from PCT/US2023/074696, mailed Apr. 3, 2025, 8 pages.
Nakamura, Yukari, PCT International Preliminary Report on Patentability and Written Opinion from PCT/US2023/018952, mailed Oct. 31, 2024, 9 pages.
Nickitas-Etienne, Athina, PCT International Preliminary Report on Patentability and Written Opinion from PCT/US2015/025176, mailed Oct. 20, 2016, 6 pages.
Tang, Xiaofan, PCT International Preliminary Report on Patentability and Written Opinion from PCT/US2022/037207, issued Dec. 18, 2024, 7 pages.
Truong, T., PCT International Search Report from PCT/US2006/011271, mailed Mar. 19, 2007, 1 page.
Wang, Xin, PCT International Preliminary Report on Patentability and Written Opinion from PCT/US2022/037210, mailed Jan. 23, 2025, 8 pages.
Hermann, P., PCT International Search Report and Written Opinion from PCT/US2023/083039, mailed Apr. 9, 2024, 12 pages.
Hill et al., "Stem cell mobilization with G-CSF induces type 17 differentiation and promotes scleroderma", Blood, 116(5), pp. 819-828 (Aug. 5, 2010).
Hirota, Keiji et al., "Regulation and function of innate and adaptive interleukin-17-producing cells", EMBO reports (2012) 13, 113-120.
Holmlin et al., "Zwitterionic SAMs that Resist Nonspecific Adsorption of Protein from Aqueous Buffer"; Langmuir, vol. 17, pp. 2841-2850 (2001).
Hudson et al., "Drug exposure during pregnancy: Current understanding and approaches to measure maternal-fetal drug exposure", Front. Pharmacol. 14:1111602, 12 pages (2023).
Hussein et al., "Inhibition of microparticle release triggers endothelial cell apoptosis and detachment", Thrombosis and Haemostasis, 98(11), pp. 1096-1107 (Jan. 1, 2007).
Imbruvica (Ibrutinib), prescribing information published 08/201 (6 pages).
Jagasia et al., "KD025 for Patients with Chronic Graft-Versus-Host Disease (cGVHD)—Long-Term Follow-up of a Phase 2a Study (KD025-208)", Blood, 134 (Supplement_1): 872 (2019) (4 pages).
Jagasia et al., "KD025-208: a Phase 2 Open-Label Trial of KD025-208 for Steroid-Dependent Chronic Graft-Versus-Host Disease (CGVHD)", Oral Presentation, Abstract S873 (Jun. 16, 2018) (2 pages).

(56) References Cited

OTHER PUBLICATIONS

Jagasia et al., "KD025-208: A Phase 2a Study of KD025 for Patients with Chronic Graft Versus Host Disease (cGVHD)—Pharmacodynamics (PD) and Updated Results", Abstracts / Biol Blood Marrow Transplant, 25(36), pp. S28-S29 (2019) (2 pages).
Jagasia et al., "KD025-208: A Phase 2a Study of KD025 for Patients with Chronic Graft Versus Host Disease (cGVHD)—Pharmacodynamics and Updated Results", Blood, 132 (Suppl_1): 602 (2018) (4 pages).
Jagasia et al., "National Institutes of Health Consensus Development Project on Criteria for Clinical Trials in Chronic Graft-versus-Host Disease: I. The 2014 Diagnosis and Staging Working Group Report", Biol Blood Marrow Transplant, 21, pp. 389-401 (2015).
Jagasia et al., "ROCK2 Inhibition With Belumosudil (KD025) for the Treatment of Chronic Graft-Versus-Host Disease", J Clin Oncol, 39, pp. 1888-1898 (2021).
Jamil et al., "State-of-the-art acute and chronic GVHD treatment", Int J Hematol, 101, pp. 452-466 (2015).
Jiang et al., "Fasudil, a Rho-Kinase Inhibitor, Attenuates Bleomycin-Induced Pulmonary Fibrosis in Mice", Int. J. Mol. Sci., 13, pp. 8293-8307 (2012).
Kadmon Corporation, LLC, Protocol No. KD025-213, Study Drug: KD025, IND No. IND 125890, NCT No. NCT03640481, "A Phase 2, Randomized, Multicenter Study to Evaluate the Efficacy and Safety of KD025 in Subjects with Chronic Graft Versus Host Disease (cGVHD) After At Least 2 Prior Lines of Systemic Therapy (The ROCKstar Study)", Last Amended Jun. 26, 2019 (10 pages).
Kadmon Corporation, Protocol No. KD025-208, Study Drug: KD025, "A Phase 2a, Dose-Escalation, Open-Label Study to Evaluate the Safety, Tolerability, and Activity of KD025 in Subjects with Chronic Graft Versus Host Disease", Last Updated Oct. 15, 2018 (10 pages).
Kemp et al., "Relationship between FEV1 decline and mortality in patients with bronchiolitis obliterans syndrome—a systematic literature review", Respiratory Medicine, 188, 106608, 8 pages (2021).
Kitko et al., "Fibrotic and Sclerotic Manifestations of Chronic Graft Versus Host Disease", Biol Blood Marrow Transplant., 18(1Suppl), pp. S46-S52 (2012).
Krishna et al., "Bronchiolitis Obliterans", StatPearls, retrieved from https://www.ncbi.nlm.nih.gov/books/NBK441865/ on Oct. 3, 2024 (6 pages).
Kuhn et al., "A Novel, High-Performance Random Array Platform for Quantitative Gene Expression Profiling"; Genome Research, 14(11); pp. 2347-2356 (2004).
Lazaryan et al., "Belumosudil for Patients with Chronic Graft-Versus-Host Disease: Combined Analysis of Failure-Free Survival (FFS) in the KD025-208 and Pivotal Rockstar Trials", Postern No. 387, Salt Palace Convention Center, Apr. 24, 2022 (5 pages).
Lazaryan et al., "Belumosudil for Patients with Chronic Graft-Versus-Host Disease: Combined Analysis of Failure-Free Survival (FFS) in the KD025-208 and Pivotal Rockstar Trials", 63rd ASH Annual Meeting Abstracts, Blood, 138, pp. 3898-3900 (2021).
Lazaryan et al., "Initial Results of KD025-208: A Phase 2a Open Label Trial of KD025 for Steroid-Dependent Chronic Graft Versus Host Disease", Blood blood, 130 (Suppl_1) : 3256 (2017) (3 pages).
Lazaryan et al., "Initial Results of KD025-208: A Phase 2a Open-Label Clinical Trial of KD025 for Steroid-Dependent Chronic Graft Versus Host Disease (cGVHD)", Abstracts / Biol Blood Marrow Transplant, 24(38), S25 (2018).
Lazaryan et al., "Reply to A. Heine et al.", Journal of Clinical Oncology, 39(29), 3308; https://doi.org/10.1200/JCO.21.01559; Published at ascopubs.org/journal/jco on Aug. 4, 2021. (2 pages).
Lee et al., "Chronic Graft-versus-Host Disease", Biology of Blood and Marrow Transplantation, 9, pp. 215-233 (2003).
Lee et al., "Measuring Therapeutic Response in Chronic Graft-Versus-Host Disease: National Institutes of Health Consensus Development Project on Criteria for Clinical Trials in Chronic Graft-Versus-Host Disease: IV. The 2014 Response Criteria Working Group Report", Biol Blood Marrow Transplant., 21(6), pp. 984-999 (2015).
Lepakhin et al., "Safety of Medicines, A guide to detecting and reporting adverse drug reactions. Why heath professionals need to take action." World Health Organization, WHO/EDM/QSM/2002.2 (20 pages) (2002).
Lianqin et al., "IRF4 and T cell differentiation and the clinical significance thereof", Chinese Journal of Immunology, vol. 28, pp. 670-672 (Jul. 20, 2012) (with English translation).
Liao, James K. MD et al., "Rho Kinase (ROCK) Inhibitors", J. Cardiovasc Phamacol, vol. 50, No. 1, Jul. 2007, 17-24.
Loher, F., PCT International Search Report and Written Opinion issued in PCT/US2025/017283, dated Jun. 12, 2025, 10 pages.
MacDonald et al., "Chronic graft-versus-host disease: biological insights from preclinical and clinical studies", Blood, 129(1), pp. 13-21 (2017).
Meyer et al., "An international ISHLT/ATS/ERS clinical practice guideline: diagnosis and management of bronchiolitis obliterans syndrome", Eur Respir J, 44, pp. 1479-1503 (2014).
Miklos et al., "Ibrutinib for chronic graft-versus-host disease after failure of prior therapy", Blood, 130(21), pp. 2243-2250 (Nov. 23, 2017).
Moyse, E., PCT International Preliminary Report on Patentability and Written Opinion from PCT/US2006/011271, mailed Sep. 25, 2007, 5 pages.
Mueller et al., "Rho Kinase, a Promising Drug Target for Neurological Disorders"; Nature Reviews Drug Discovery, vol. 4, pp. 387-398 (2005).
Murata et al.,"Inhibitory effect of Y-27632, a ROCK inhibitor, on progression of rat liver fibrosis in association with inactivation of hepatic stellate cells" Journal of Hepatology, 35(4), pp. 474-481 (2001).
Nikolaenko et al., "Graft-Versus-Host Disease in Multiple Myeloma Patients Treated With Daratumumab After Allogeneic Transplantation", Clinical Lymphoma, Myeloma & Leukemia, 20(6), pp. 407-414 (2020).
Notice of opposition to a European patent filed by Elkington and Fife LLP on Feb. 28, 2023 for EP Patent No. EP2903618, 5 pages.
Notice of Opposition to a European patent filed by Sandoz AG on Feb. 28, 2023 for EP Patent No. EP2903618, 6 pages.
Office Action dated May 23, 2017 from Japanese Application No. 2015-535880, including English translation, 7 pages.
Orange Book: Approved Drug Products with Therapeutic Equivalence Evaluations, Product Details for NDA 214783, Rezurock (Belumosudil Mesylate), Approved Jul. 16, 2021, 1 page.
Ostuni et al., "Self-Assembled Monolayers that Resist the Adsorption of Proteins and the Adhesion of Bacterial and Mammalian Cells"; Langmuir, vol. 17, pp. 6336-6343 (2001).
Pang et al., "The ISHLT chronic lung allograft dysfunction consensus criteria are applicable to pulmonary chronic graft-versus-host disease", Blood Advances, 6(14), pp. 4196-4207 (Jul. 26, 2022).
Pidala et al., "Patient-reported quality of life is associated with severity of chronic graft-versus-host disease as measured by NIH criteria: report on baseline data from the Chronic GVHD Consortium", Blood, 117(17), pp. 4651-4657 (Apr. 28, 2011).
Press release on: https://piplinereview.com/index.php/, "Kadmon Announces First Patient Dosed in Phase I Study of Selective ROCK2 Inhibitor KD025", Small Molecules News Channel, Feb. 27, 2012 (1 page).
Ravaglia et al., "Bronchiolitis and Bronchiolar Disorders", Semin Respir Cri Care Med, 41, pp. 311-332 (2020).
Rikitake et al., "Inhibition of Rho Kinase (ROCK); Leads to Increased Cerebral Blood Flow and Stroke Protection"; Stroke, 36(10), pp. 2251-2257 (2005).
Roche Lexikon Medizin, Medical Dictionary, catchwords., Ekzem "and . . . Dermatitis" (1987) (5 pages).
Rodriguez-Palmero, M., Extended European Search Report from EP22183286.8 mailed Jan. 16, 2023, 7 pages.
Rodriguez-Palmero, M., PCT International Search Report and Written Opinion from PCT/US2023/018952, mailed Jul. 27, 2023, 13 pages.
Rokosz et al., "Kinase inhibitors as drugs for chronic inflammatory and immunological diseases: progress and challenges", Expert Opin. Ther. Targets, 12(7), pp. 883-903 (2008).

(56) References Cited

OTHER PUBLICATIONS

Rossi et al., "Mouse models of multiple myeloma: technologic platforms and perspectives", Oncotarget, 9(28), pp. 20119-20133 (2018).
Rotta et al., "Impact of Recipient Statin Treatment on Graft-versus-Host Disease after Allogeneic Hematopoietic Cell Transplantation", Biology of Blood and Marrow Transplantation, 16(10), pp. 1463-1466 (Oct. 1, 2010).
Sachdeva et al., "Drug Use in Pregnancy; a Point to Ponder!", Indian Journal of Pharmaceutical Sciences, vol. 71, pp. 1-7 (2009).
Saillard et al., "National Institutes of Health classification for chronic graft-versus-host disease predicts outcome of allo-hematopoietic stem cell transplant after fludarabine-busulfan-antithymocyte globulin conditioning regimen", Leukemia & Lymphoma, vol. 55, pp. 1106-1112 (2014).
Sala-Torra et al., "Serious acute or chronic graft-versus-host disease after hematopoietic cell transplantation: a comparison of myeloablative and nonmyeloablative conditioning regimens", Bone Marrow Transplantation, 41, pp. 887-893 (2008).
Salhotra et al., "KD025-208: a Phase 2A Trial of KD025 for Patients With Chronic Graft-Versus-Host Disease (CGVHD)—Updated Safety and Efficacy", HemaSphere, 3:S1(PS1533), pp. 707-708 (2019).
Sasaki et al., "Transcellular Transport of Organic Anions Across a Double-Transfected Madin-Darby Canine Kidney II Cell Monolayer Expressing Both Human Organic Anion-Transporting Polypeptide (OATP2/SLC21A6) and Multidrug Resistance-Associated Protein 2 (MRP2/ABCC2)", Journal of Biological Chemistry, 277(8), pp. 6497-6503 (2002).
Scheithe, R., PCT International Search Report and Written Opinion from PCT/US2024/038315, mailed Oct. 25, 2024, 14 pages.
Schutt et al., "Inhibition of BTK and ITK with Ibrutinib is Effective in the Prevention of Chronic Graft-versus-Host Disease in Mice", PLOS One, 10(9), e0137641 (Sep. 8, 2015) (17 pages).
Sennino et al., "Sequential Loss of Tumor Vessel Pericytes and Endothelial Cells after Inhibition of Platelet-Derived Growth Factor B by Selective Aptamer AX102", Cancer Res., 67(15), pp. 7358-7367 (2007).
Serody et al., "The IL-17 Differentiation Pathway and Its Role in Transplant Outcome", Biol Blood Marrow Transplant, 18, pp. S56-S61 (2012).
Sheen et al., "Bioavailability of a Poorly Water-Soluble Drug from Tablet and Solid Dispersion in Humans"; Journal of Pharmaceuticals Sciences, 80(7), pp. 712-714 (1991).
Statement of Opposition filed by Elkington and Fife LLP on Feb. 28, 2023 for EP Patent No. EP2903618, 12 pages.
Statement of Opposition filed by Sandoz AG on Feb. 28, 2023 for EP Patent No. EP2903618, 21 pages.
Teh et al., "Reliability and validity of the modified 7-day Lee Chronic-versus-Host Disease Symptom Scale", Biol Blood Marrow Transplant, 26(3), pp. 562-567 (2020).
Tesmer et al., "Th17 cells in human disease", Immunological Reviews, 223, pp. 87-113 (2008).
Third Office action from CN 201380063599.7, issued on Sep. 25, 2018, including English translation; 15 pages.
Thomas et al., "Lung Transplantation Mini-Series #4, Bronchiolitis Obliterans Syndrome (BOS) Following Lung Transplant", Am J. Respir Crit Care Med, vol. 193, pp. P19-P20 (2016).
U.S. Department of Health and Human Services, "S5 (R3) Detection of Reproductive and Developmental Toxicity for Human Pharmaceuticals, Guidance for Industry", May 2021, Revision 3, 124 pages.
U.S. Department of Health and Human Services, Common Terminology Criteria for Adverse Events (CTCAE), Version 4.03, Jun. 14, 2010, 80 pages.
U.S. Department of Health and Human Services, Common Terminology Criteria for Adverse Events (CTCAE), Version 5.0, Nov. 27, 2017, 155 pages.
Urisman et al., "Small Airway Disease: A Step Closer to Etiology-Based Classification of Bronchiolitis", Surgical Pathology, 13, pp. 189-196 (2020).
Venturini, F., PCT International Search Report and Written Opinion from PCT/US2023/080712, mailed Jun. 26, 2024, 11 pages.
Verleden et al., "Chronic lung allograft dysfunction: Definition, diagnostic criteria, and approaches to treatment—A consensus report from the Pulmonary Council of the ISHLT", The Journal of Heart and Lung Transplantation, 38(5), pp. 493-503 (2019).
Verleden et al., "Chronic lung allograft dysfunction: light at the end of the tunnel", Curr Opin Organ Transplant, 24(3), pp. 318-323 (2019).
Visscher et al., "Bronchiolitis The Pathologist's Perspective", Proc Am Thorac Soc, vol. 3, pp. 41-47 (2006).
Weisdorf et al., "KD025 for Patients with Chronic Graft-Versus-Host Disease (cGVHD) Long-Term Follow-up of a Phase 2a Study (KD025-208)", Abstracts / Biol Blood Marrow Transplant, 26(275), p. S187-S188 (2020).
Wikipedia, "Rho-Associated Protein Kinase", http:/fen.wikipedia.org/wiki/Rho-associated_protein_kinase, pp. 1-6 (2011).
Williams et al., "Fluticason, Azithromycin, and Montelukast Treatment for New-Onset Bronchiolitis Obliterans Syndrome after Hematopoietic Cell Transplantation", Biol Blood Marrow Transplant., (2016), 22(4), pp. 710-716.
Williams et al., "How I treat bronchiolitis obliterans syndrome after hematopoietic stem cell transplantation", Blood, 129(4), pp. 448-455 (2017).
Willson et al., "Taste Assessment Study of Belumosudil to Inform an Integrated Pediatric Formulation Development Program", 13th Annual Conference European Pediatric Formulation Initiative; EUPFI 2021; 1 page, Retrieved from the Internet: URL:https://www.quotientsciences.com/media/uploads/files/Quotient_-_Taste_Assessment_Study_of_Belumosudil_to_Inform_an_Integrated_Paediatric_Formulation_Development_Program_-_Kadmon_EuPFI_-_Clinical_Poster_-_Sep. 21.pdf [retrieved on Apr. 25, 2023].
Wingard et al., "Long-Term Survival and Late Deaths After Allogeneic Hematopoietic Cell Transplantation", Journal of Clinical Oncology, 29(16), pp. 2230-2239 (2011).
Wong et al., "Long-term recovery after hematopoietic cell transplantation: predictors of quality-of-life concerns", Blood, 115(12), pp. 2508-2519 (2010).
Young, L.W., PCT International Search Report and Written Opinion from PCT/US2013/063752, mailed Apr. 24, 2014, 10 pages.
Young, L.W., PCT International Search Report and Written Opinion from PCT/US2015/025176, mailed Jun. 26, 2015, 7 pages.
Yusen et al., "The Registry of the International Society for Heart and Lung Transplantation: Thirty-first Adult Lung and Heart-Lung Transplant Report—2014; Focus Theme: Retransplantation", The Journal of Heart and Lung Transplantation, 33(10), pp. 1009-1024 (2014).
Zanin-Zhorov et al., "Selective oral ROCK2 inhibitor down-regulates IL-21 and IL-17 secretion in human T cells via STAT3-dependent mechanism", PNAS, 111(47), pp. 16814-16819 (Nov. 25, 2014).
Zeiser et al., "Pathophysiology of Chronic Graft-versus-Host Disease and Therapeutic Targets", New England Journal of Medicine, 377, pp. 2565-2579 (2017).
Zeiser et al., "Three US Food and Drug Administration-approved therapies for chronic GVHD", Blood, 139(11), pp. 1642-1645 (2022).
Zeiser, Clinical Advances in Hematology and Oncology, vol. 19, pp. 1-24 (2021).
Anonymous, "CTCAE and Adverse Event Reporting", Nat'l Cancer Inst. Div. of Cancer Treatment & Diagnosis, last updated Sep. 2, 2025, retrieved from https://dctd.cancer.gov/research/ctep-trials/for-sites/adverse-events, 6 pages.
Anonymous: Highlights of Prescribing Information: Rezurock (TM) (belumosudil) tablets, for oral use; Initial U.S. Approval: 2021, Revised: Dec. 2024, 6 pages.
Business Wire, "Kadmon Pharmaceuticals and Nano Terra Announce Worldwide Exclusive Licensing Agreement for Three Novel Product Candidates", BioSpace, Apr. 25, 2011, retrieved from https://www.biospace.com/b-kadmon-pharmaceuticals-b-and-b-nano-terra-b-announce-worldwide-exclusive-licensing-agreement-for-three-novel-product-candidates, 10 pages.

(56) References Cited

OTHER PUBLICATIONS

Cutler, Corey S., "Dr. Cutler on the Toxicity Profile of Belumosudil in cGVHD", Mar. 17, 2021, OncLive, retrieved from https://www.onclive.com/view/dr-cutler-on-the-toxicity-profile-of-belumosudil-in-cgvhd, 5 pages.
Ellis, James et al., "ROCK-2 Selective Inhibitors for the Treatment of Oncology and Fibrotic Disease", Inflamm. Res., Supplement 3 (2007), S345, 1 page.
Fan, Daiming, ed., Frontiers in Tumor Research, Cancer Research Frontier, vol. 11, Chapter 9, pp. 161-162 (Dec. 31, 2011), with English translation (24 pages).
Gottardi, Francesca et al., "Treatment of steroid-refractory graft versus host disease in children", Front. Transplant. 2.1251112, 2023, 18 pages.
Heine et al., "ROCKing Chronic Graft-Versus-Host Disease", American Society of Clinical Oncology, 39(29), 3308 (https://doi.org/10.1200/JCO.21.01081; Published at ascopubs.org/journal/jco on Aug. 4, 2021 (2 pages).
Liu, Ruyi, et al., ed., Xian Jiaotong University Press, Clinical Immunology, Chapter 13, p. 193 (Aug. 31, 2008), with English translation (27 pages).
Nanowerk News, "Kadmon Pharmaceuticals and Nano Terra Announce Worldwide Exclusive Licensing Agreement for Three Novel Product Candidates", The Wayback Machine Archive, posted on Apr. 25, 2011, 2 pages, obtained from https://web.archive.org/web/20110430005648/http://www.nanowerk.com/news/newsid=21135.php.
Silva Franco et al., "Drug Repurposing by Virtual Screening: Identification of New Already Approved ROCK Inhibitors as Promising Drugs to Target Neurodegeneration", ACS Omega, 10, pp. 28446-28465 (2025).
Vogelsang, Georgia B., "How I treat chronic graft-versus-host disease", Blood, Mar. 1, 2001, vol. 97, No. 5, 1196-1201.
"Follow-Up Analysis of KD025-213 (the ROCKstar study): A Phase 2, Randomized, Multicenter Study to Evaluate the Efficacy and Safety of KD025 in Patients With cGVHD", Clinical Advances in Hematology & Oncology, 19(2), Supplement 8, pp. 8-10 (Feb. 2021).
Abedin et al., "Predictive Value of Bronchiolitis Obliterans Syndrome Stage Op in Chronic Graft-versus-Host Disease of the Lung", Biol Blood Marrow Transplant. Jun. 2015; 21(6): 1127-1131.
Aguilar et al., "Obliterative Bronchiolitis", Transplantation 2016; 100(2); 272-283.
Ahn et al., "Prognostic role of FEV1 for survival in bronchiolitis obliterans syndrome after allogeneic hematopoietic stem cell transplantation", Clinical Transplantation 2015, 29(12): 1133-1139.
Ali et al., "Belumosudil with ROCK-2 inhibition: chemical and therapeutic development to FDA approval for the treatment of chronic graft-versus-host disease", Current Research in Translational Medicine, 70, 103343 (2022) (12 pages).
Anomymous, "Study Details: KD025 Hepatic Impairment Study with Normal Hepatic Function and Subjects With Varying Degrees of Hepatic Impairment", ClinicalTrials.gov, Jul. 18, 2022, retrieved from the internet: https://clinicaltrials.gov/study/NCT04166942?intr=NCT04166942&rank=1, 15 pages.
Anonymous, "Rezurock 200 mg film-coated tablets—Summary of Product Characteristics (SmPC)", Sep. 2, 2022, 12 pages, retrieved from the Internet: URL:https://www.medicines.org.uk/emc/product/14659/smpc/print [retrieved on Apr. 22, 2023].
Anonymous, Belumosudil Dosage Guide & Max Dose, Adjustments, Drugs [online]; 2022; published Jun. 21, 2022; downloaded from on Aug. 10, 2023; 3 pages. (Year: 2022).
Anonymous, Rezurock: Uses, Dosage, Side Effects, Warnings, Drugs [online]; 2021; downloaded from on Aug. 10, 2023; 4 pages. (Year: 2021).
Anonymous: Highlights of Prescribing Information: IMBRUVICA (R) (ibrutinib) capsules, for oral use; IMBRUVICA (R) (ibrutinib) tablets, for oral use; Revised Apr. 2020, 58 pages.
Anonymous: Highlights of Prescribing Information: JAKAFI (R) (ruxolitinib) tablets, for oral use; Revised May 2019 2011, 39 pages.
Arjuna et al., "An update on current treatment strategies for managing bronchiolitis obliterans syndrome after lung transplantation", Expert Rev Resp Med., 15(3), pp. 339-350 (Mar. 2021).
Arora et al., "Late Acute and Chronic Graft-versus-Host Disease after Allogeneic Hematopoietic Cell Transplantation", Biol Blood Marrow Transplant, 22(3), pp. 449-455 (2016).
Ashburner, et al., "Gene Ontology Tool for the Unification of Biology"; Nature Genetics (2000)1 vol. 25:1; pp. 25-29.
Baird et al., "Chronic Graft Versus Host Disease (GVHD) in Children", Pediatr Clin North Am., 57(1), pp. 297-322 (Feb. 2010).
Barbour et al., "Effect of Hepatic Impairment on the Pharmacokinetics of Itacitinib", The Journal of Clinical Pharmacology, 61(7), pp. 954-960 (2021).
Benbow, S., PCT International Search Report and Written Opinion from PCT/US2023/074696, mailed Dec. 19, 2023, 11 pages.
Benbow, S., PCT International Search Report from PCT/US2022/044256, mailed May 8, 2023, 11 pages.
Berge et al., "Pharmaceutical Salts", Journal of Pharmaceuticals Sciences, 66(1), pp. 1-19 (1977).
Bergeron et al., "Budesonide/Formoterol for Bronchiolitis Obliterans after Hematopoietic Stem Cell Transplantation", Am J Respir Crit Care Med, 191(11), pp. 1242-1249 (2015).
Beville et al., "Development of a Novel Pediatric Belumosudil Oral Suspension", 13th Annual Conference European Pediatric Formulation Initiative; EUPFI 2021; 1 page, Retrieved from the Internet: URL:https://www.quotientsciences.com/media /uploads/files/Development_of_a_novel_pediatric_belumosudil_oral_suspension-_Quotient_Sciences_EuPFI_Poster_2021.pdf [retrieved on Apr. 25, 2023].
Biswas et al., "Aberrant ROCK activation promotes the development of type I diabetes in NOD mice", Cell Immunol., 266(2), pp. 111-115 (2011).
Biswas et al., "Phosphorylation of IRF4 by ROCK2 regulates IL-17 and IL-21 production and the development of autoimmunity in mice", The Journal of Clinical Investigation, vol. 120, No. 9, Sep. 2010, 3280-3295.
Brownback et al., "Effect of extracorporeal photopheresis on lung function decline for severe bronchiolitis obliterans syndrome following allogeneic stem cell transplantation", J Clin Apher, 31(4), pp. 347-352 (2016).
Brownback et al., "Effect of Rituximab on Pulmonary Function in Bronchiolitis Obliterans Syndrome due to Graft-Versus-Host-Disease", Lung, 195(6), pp. 781-788 (2017).
Chapman et al., "Surveying for Surfaces that Resist the Adsorption of Proteins", J_ Am. Chem. Soc., vol. 122, pp. 8303-8304 (2000).
Church, "Livestock Feeds and Feeding"; (1977); O & A Books (6 pages).
Clinical Trial NCT02841995, "A Study to Evaluate the Safety, Tolerability, and Activity of KD025 in Subjects With Chronic Graft Versus Host Disease", established Jul. 22, 2016 (9 pages).
ClinicalTrials.gov ID No. NCT02841995, "A Study to Evaluate the Safety, Tolerability, and Activity of KD025 in SubjectsWith Chronic Graft Versus Host Disease", Last Updated Jun. 28, 2023 (14 pages).
ClinicalTrials.gov ID No. NCT03640481, "Efficacy and Safety of KD025 in Subjects With cGVHD After At Least 2 PriorLines of Systemic Therapy", Record History Tab, Last Updated Jun. 22, 2021 (22 pages).
Clinicaltrials.gov, History of Changes for Study: NCT03640481, Aug. 17, 2018, "Efficacy and Safety of KD025 in Subjects with cGVHD After At Least 2 Prior Lines of Systemic Therapy", retrieved from https://clinicaltrials.gov/ct2/history/NCT03640481?V_1=View#StudyPageTop (7 pages).
Clinicaltrials.gov, NCT03640481: Efficacy and Safety of KD025 in Subjects With cGVHD After At Least 2 Prior Lines of Systemic Therapy, Mar. 9, 2022, Study Details Tab, retrieved from the internet: https://classic.clinicaltrials.gov/ct2/show/NCT03640481 (28 pages).
Collins, S., PCT International Search Report and Written Opinion from PCT/US2024/049962, mailed Jan. 3, 2015, 11 pages.
Cutler et al., "Belumosudil for Chronic Graft-Versus Host Disease After 2 or More Prior Lines of Therapy: The ROCKstar Study (KD025-213)", EHA Library, Abstract: S239 (Jun. 9, 2021) (2 pages).

(56) References Cited

OTHER PUBLICATIONS

Cutler et al., "Belumosudil for Chronic Graft-Versus-Host Disease (cGVHD) after 2 or More Prior Lines of Therapy: The Rockstar Study (KD025-213)", Abstracts / Transplant Cell Ther 27 3S, 9, pp. S7-S8 (2021).
Cutler et al., "Belumosudil for Chronic Graft-Versus-Host Disease (cGVHD) after 2 or More Prior Lines of Therapy: The Rockstar Study (KD025-213)", Blood, 136 (Supplement 1): 45 (2020) (5 pages).
Cutler et al., "Belumosudil for chronic graft-versus-host disease after 2 or more prior lines of therapy: the ROCKstar Study", Blood, vol. 138, No. 22, pp. 2278-2289 (2021).
Cutler et al., "LBA2—Interim Analysis of KD025-213: A Phase 2, Randomized, Multicenter Studyto Evaluate the Efficacy and Safety of KD025 in Subjects with Chronic Graft VersusHost Disease (cGVHD) after at Least 2 Prior Lines of Systemic Therapy (TheROCKstar Study; NCT03640481)", World Center Marriott—Palms: Royal, Feb. 23, 2020 (5 pages).
Cutler et al., "Mechanistic approaches for the prevention and treatment of chronic GVHD", Blood, 129(1), pp. 22-29 (Jan. 5, 2017).
Cutler, Corey, "Treating Inflammation and Fibrosis in Chronic GVHD: Two Birds, One ROCK", Journal of Clinical Oncology, 39(17), pp. 1942-1946 (2021).
Defilipp et al., "Clinical response to belumosudil in bronchiolitis obliterans syndrome: a combined analysis from 2 prospective trials", Blood Advances, 6(24), pp. 6263-6270 (Dec. 27, 2022).
Dordunoo et al., "Preformulation Studies on Solid Dispersions Containing Triamterene or Temazepam in Polyethylene Glycols or Gelucire 44/14 for Liquid Filling of Hard Gelatin Capsules", Drug Development and Industrial Pharmacy, 17(12), pp. 1685-1713 (1991).
Flowers et al., "How we treat chronic graft-versus-host disease", Blood, 125(4), pp. 606-615 (2015).
Flynn et al., "Targeted Rho-associated kinase 2 inhibition suppresses murine and human chronic GVHD through a Stat3-dependent mechanism", Blood, 127(17), pp. 2144-2154 (Apr. 28, 2016).
Gerber, M., PCT International Search Report and Written Opinion from PCT/US2023/081268, mailed Feb. 16, 2024, 15 pages.
Goodman & Gilman, "The Pharmacological Basis of Therapeutics" (9th ed, 1996); 29 pgs.
Grampton et al., "Applied Animal Nutrition"; WH Freedman and Company (1969); 2nd ed., 14 pages.
Greene et al., "Protective Groups in Organic Synthesis"; Wiley-Interscience (1991), 2nd ed. (4 pages).
Greene et al., "Protective Groups in Organic Synthesis"; Wiley-Interscience (1999), 3rd ed. (84 pages).
Herman, P., Extended European Search Report from EP23305096.2, mailed Jul. 21, 2023, 11 pages.
ClinicalTrials.gov ID No. NCT04930562, "Efficacy and Safety of BN101 in Subjects With Chronic Graft Versus Host Disease (cGVHD)", Record History ver. 5-6: 2023-10-08, Last Updated Jan. 17, 2024 (43 pages).
Kharkevich, D.A., Pharmacology/Textbook, 2010, 10th edition, pp. 72-82, including English translation.
Linlin DAI., Statistical Analysis Plan, A Phase 2, Open-label, Multicenter Study to Evaluate the Efficacy and Safety of BN101/belumosudil in Subjects with Chronic Graft Versus Host Disease (cGVHD) After at Least 1 Priority Line of Systemic Therapy, dated Jun. 17, 2022, pp. 1-24, retrieved from the internet https://cdn.clinicaltrials.gov/large-docs/62/NCT04930562/SAP_001.pdf (Uploaded to Clinicaltrials.gov NCT04930562 on Oct. 8, 2023).
The Synopsis of BN101-201 Protocol (Clinical Study Protocol NCT04930562), A Phase 2, Open-label, Multicenter Study to Evaluate the Efficacy and Safety of BN101/belumosudil in Subjects with Chronic Graft Versus Host Disease (cGVHD) After at Least 1 Priority Line of Systemic Therapy, dated Feb. 25, 2022, pp. 1-118, retrieved from the internet https://cdn.clinicaltrials.gov/large-docs/62/NCT04930562/Prot_002.pdf (Uploaded to Clinicaltrials.gov NCT04930562 on Dec. 3, 2023).
The Synopsis of BN101-201 Protocol (Protocol Synopsis NCT04930562), A Phase 2, Open-label, Multicenter Study to Evaluate the Efficacy and Safety of BN101/belumosudil in Subjects with Chronic Graft Versus Host Disease (cGVHD) After at Least 1 Priority Line of Systemic Therapy, dated Feb. 25, 2022, pp. 1-14, retrieved from the internet https://cdn.clinicaltrials.gov/large-docs/62/NCT04930562/Prot_000.pdf (Uploaded to Clinicaltrials.gov NCT04930562 on Sep. 22, 2023).
Anonymous, "AHFS first Release Belumosudil Mesylate," Am J Health Syst Pharm, Nov. 2021, vol. 78, No. 22, pp. 2002-2004.
Belikov, V.G., "Pharmaceutical Chemistry," textbook, 2007, Moscow, MEDpress-inform, pp. 27-29, with English translation of pp. 27-29; 10 pages.
Blair "Belumosudil: First Approval," Drugs, 2021, V.81, pp. 1677-1682, [found online], [found 21.05.2026], retrieved from the Internet: https://pmcncbi.nlm.nih.gov/articles/PMC8590654/pdf/40265_2021_Article_1593.pdf.
ClinicalTrials.gov ID No. NCT05305989, "Extended Treatment and Follow-up of Subjects Treated With Belumosudil in Study KD025-208 or Study KD025-213," Record History ver. 5: Jun. 27, 2022, Last Updated May 2, 2025 (12 pages).
Duess, et al., "Teratogenesis in the chick embryo following post-gastrulation exposure to Y-27632 -effect of Y-27632 on embryonic development", Toxicology and Applied Pharmacology, vol. 409, 115277, pp. 1-14. Published online Oct. 10, 2020.
Imbruvica (Ibrutinib), prescribing information published Jan. 2019 (6 pages).
Kono et al. "Inhibition of RHO-ROCK signaling enhances ICM and suppresses TE characteristics through activation of Hippo signaling in the mouse blastocyst", Dev Biol. 394(1): 142-155, Oct. 1, 2014.
Meredith P.A., "Substitution of original medicinal products with generics: bioequivalence and therapeutic equivalenceof various amlodipine salts," Russian Medical Journal, 2009, vol. 18 (1150), [found online], [found on Dec. 11, 2024], retrieved from the Internet: https://www.rmj.ru/articles/kardiologiya/Zamena_originalynyh_medikamentoznyh_preparatov_na_generiki_bioekvivalentnosty_i_terapeuticheskaya_ekvivalentnosty_razlichnyh_soley_amlodipina/?utm_source=google.com&utm_medium=organic&utm_campaign=google.
Rezurock (belumosudil) dosing, indications, interactions, adverse effects, and more. Jul. 25, 2021. https://reference.medscape.com/drug/rezurockbelumosudil-4000186#0; 16 pages.
Saadeldin et al. "Rocking the Boat: The Decisive Roles of Rho Kinases During Oocyte, Blastocyst, and Stem Cell Development", Front. Cell Dev. Biol. 8:616762, pp. 1-10, published online Jan. 11, 2021.
Borisova, E.O., "Fundamentals of Pharmacokinetics," School for Practicing Physicians, Clinical Pharmacology, Handbook for the Outpatient Physicians, No. 6, 2014, pp. 44-51, including English translation.

O-dealkylated belumosudil sulfate
11.5% (plasma), 5.0% (urine),
34.7% (feces)*

O-dealkylated
Belumosudil
<2% (plasma)* belumosudil glucuronide
14.6% (plasma),
72.8% (urine)

dihydroxy belumosudil
7.8% (urine), 4.2%
(feces)

belumosudil (KD025)
64.2% (plasma), 29.6%
(feces)

KD025m2
11.5% (plasma), 5.0% (urine),
34.7% (feces)* monohydroxy belumosudil
11.1% (feces)

belumosudil diol
9.9% (feces)

monohydroxy belumosudil
3.7% (plasma)

KD025m1
<2% (plasma)

BELUMOSUDIL METABOLITES AND USES THEREOF IN THE TREATMENT OF CHRONIC GRAFT-VERSUS-HOST DISEASE

CROSS-REFERENCE TO RELATED APPLICATIONS

This application is a divisional of U.S. application Ser. No. 18/105,427, filed Feb. 3, 2023, which is a continuation of International Application No. PCT/US2022/037210, filed Jul. 14, 2022, the entire contents of which are incorporated by reference herein for all purposes.

TECHNICAL FIELD

The present disclosure relates to metabolites of belumosudil and to use of said metabolites to treat autoimmune disorders in patients including for the treatment of chronic graft-versus-host disease (cGVHD).

BACKGROUND

Chronic graft-versus-host disease (cGVHD) is an immune-mediated inflammatory and fibrotic disorder. It is a potential, serious complication following solid organ transplant and allogeneic hematopoietic cell transplant (alloHCT). cGVHD affects up to 70% of all alloHCT recipients, with an incidence of 20%-50% in children. It is the leading cause of non-relapse mortality beyond 2 years after alloHCT. The estimated prevalence of cGVHD is 14,000 patients in the United States (as of 2016). (Bachier C R et al: *Epidemiology and real-world treatment of chronic graft-versus-host disease post allogeneic hematopoietic cell transplantation: A US claims analysis*. Presented at ASH 2019, Orlando, FL, Dec. 7-10, 2019) ("Bachier et al.")

Patients with cGVHD have substantial impairment in quality of life (QOL) as assessed by the Lee Symptom Scale (LSS), which measures the effect of cGVHD on patients' functioning and well-being. It is reported that only one third of patients who have cGVHD and start systemic treatment will be alive, in remission and off immunosuppressive therapy by 5 years. (Lee S J et al: *Success of immunosuppressive treatments in patients with chronic graft-versus-host disease*. Biol Blood Marrow Transpl 24:555-562, 2018) ("Lee et al.").

The pathophysiology of cGVHD can be separated into three phases: early inflammation because of tissue injury, a dysregulated adaptive immune system, and chronic inflammation and aberrant tissue repair with fibrosis.

First-line therapy for National Institutes of Health (NIH)-defined moderate to severe chronic graft-versus-host disease (cGVHD) is corticosteroids alone or in combination with sirolimus or a calcineurin inhibitor. However, up to 70% of patients require additional lines of therapy. (Bachier C R et al). Furthermore, the long-term use of corticosteroids is associated with significant side effects. (Lee et al).

Management of cGVHD continues to evolve with the advent of targeted therapies. cGVHD is characterized by an overproduction of proinflammatory cytokines IL-21 and IL-17, as well as overactivation of T follicular helper cells and B cells, which in turn leads to overproduction antibodies.

In 2017, the US Food and Drug Administration approved ibrutinib, a Bruton's Tyr kinase inhibitor, for the treatment of adults with cGVHD after failure of one or more 1 systemic lines of therapy. In patients with cGVHD who were required to have either >25% body surface area erythematous rash or an NIH mouth score of >4, a study with ibrutinib reported an overall response rate (ORR) of 67% and a discontinuation rate because of treatment-emergent adverse events (TEAEs) of 43%. (Waller E K, et al: *Ibrutinib for chronic graft-versus-host disease after failure of prior therapy: 1-Year update of a phase 1b 2 study*. Biol Blood Marrow Transpl 25:2002-2007, 2019).

There remains an opportunity to study other treatment options for patients with cGVHD, including those who have failed ≥1 lines of therapy.

SUMMARY

The present disclosure provides metabolites of belumosudil and use of the metabolites to treat ROCK2 mediated diseases in patients including treatment of autoimmune disorders such as cGVHD. In one embodiment, the present disclosure comprises use of the compound 2-(3-(4-(1H-indazol-5-ylamino)quinazolin-2-yl)phenoxy)acetamide to treat autoimmune disorders, in some embodiments, to treat cGVHD.

The present disclosure further provides belumosudil metabolites, or pharmaceutically acceptable salts thereof, in isolated form, as well as their use to treat autoimmune disorders, in some embodiments, to treat cGVHD. The disclosure provides an isolated or synthesized compound comprising belumosudil glucuronide, O-dealkylated belumosudil sulfate, monohydroxy belumosudil, and/or belumosudil diol, or a pharmaceutically-acceptable salt thereof.

The present disclosure further provides the metabolic pathway for belumosudil, for use in preparing a medicament for the treatment of an autoimmune disease in a subject. Use of the belumosudil metabolites disclosed herein, and/or the metabolic pathway for belumosudil, are useful in preparing a protocol for the treatment of an autoimmune disease in a subject.

The present embodiments can be understood more fully by reference to the detailed description and examples, which are intended to exemplify non-limiting embodiments.

DETAILED DESCRIPTION

Overview

Figure 1:
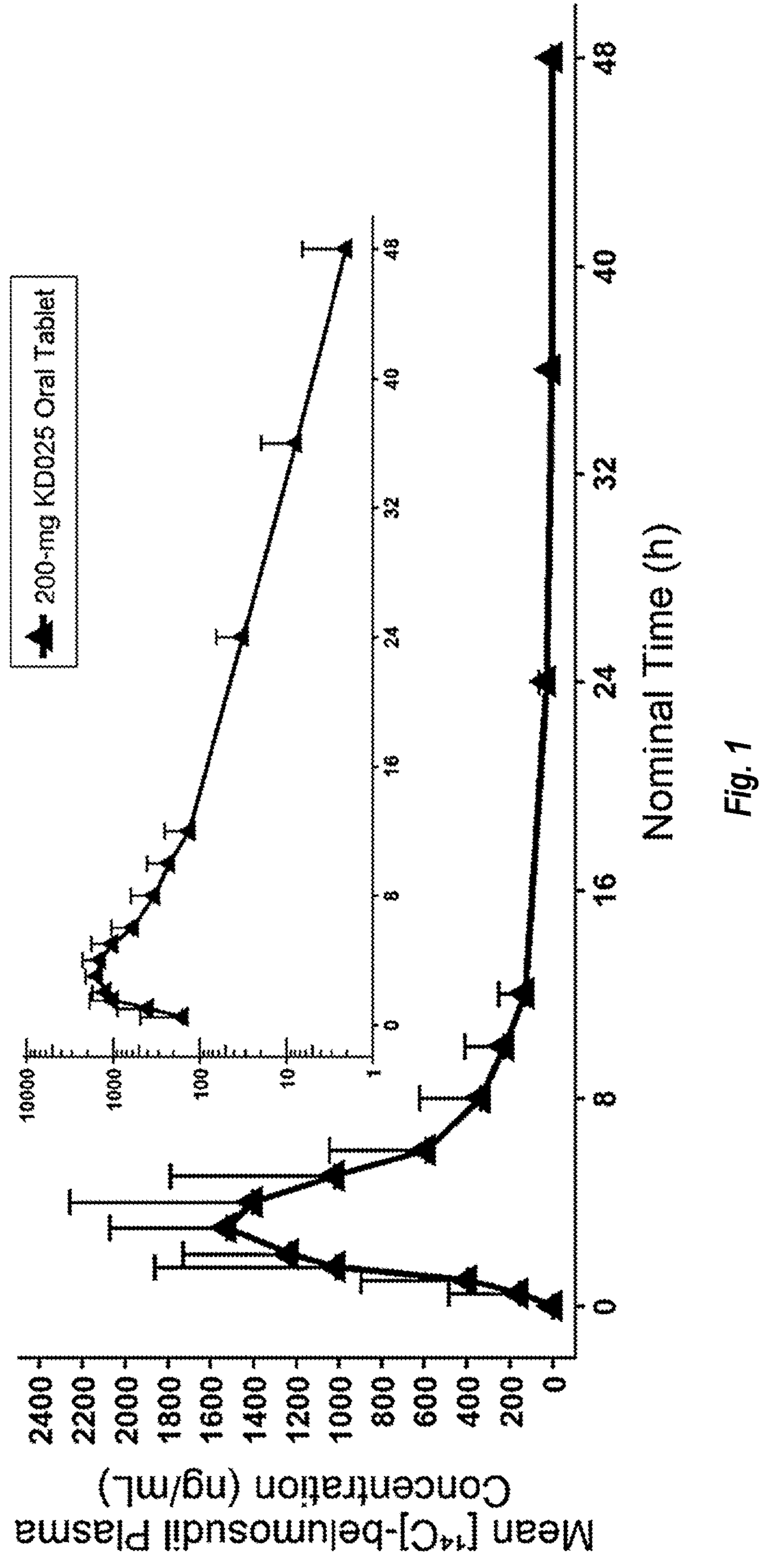
FIG. 1 is a graph showing mean PK profiles for unlabeled belumosudil after administration of a single 200-mg dose of belumosudil followed by a 15-minute [$^{14}$C]-belumosudil IV infusion. The inset graph shows the data on a log-linear scale.

Belumosudil is an oral selective rho-associated coiled-coil-containing protein kinase-2 (ROCK2) inhibitor. ROCK2 inhibition acts on the dysregulated adaptive immune system and the fibrosis that occurs because of aberrant tissue repair. Belumosudil inhibits ROCK2 and ROCK1 with $IC_{50}$ values of approximately 100 nM and 3 μM, respectively. Belumosudil down-regulated proinflammatory responses via regulation of STAT3/STAT5 phosphorylation and shifting Th17/Treg balance in ex-vivo or in vitro-human T cell assays. Belumosudil also inhibited aberrant pro-fibrotic signaling, in vitro. In vivo, belumosudil demonstrated activity in animal models of chronic GVHD.

The compound belumosudil has the chemical name: 2-{3-[4-(1H-indazol-5-ylamino)-2-quinazolinyl]phenoxy}-N-(propan-2-yl) acetamide. The compound belumosudil is also known as KD025. The mesylate salt of belumosudil is marketed as REZUROCK™ in the United States and other countries for the treatment of patients with chronic GVHD (cGVHD), in some instances after failure of at least two prior lines of systemic therapy. The active pharmaceutical ingredient of REZUROCK™ is belumosudil mesylate salt with the molecular formula $C_{27}H_{28}N_6O_5S$, a molecular weight of 548.62 g/mol, and having the chemical name 2-{3-[4-(1H-indazol-5-ylamino)-2-quinazolinyl]phenoxy}-N-(propan-2-yl) acetamide methanesulfonate (1:1).

The chemical structure of belumosudil mesylate is as follows:

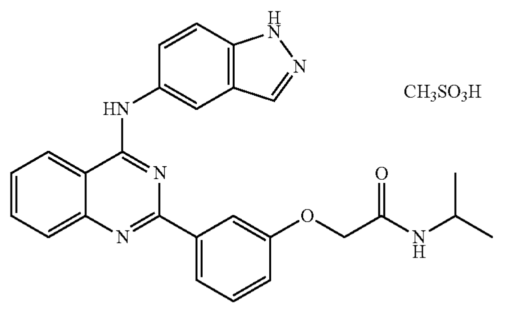 [SMILES: CC(C)NC(=O)COc1cccc(-c2nc(Nc3ccc4[nH]ncc4c3)c3ccccc3n2)c1 ; "CH3SO3H"]

The chemical structure of radiolabeled belumosudil as used in the study in Example 1 has the structure:

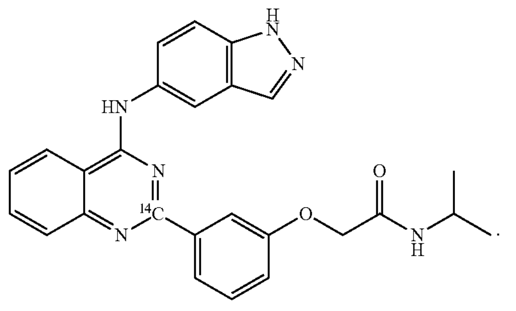 [SMILES: CC(C)NC(=O)COc1cccc(-[14c]2nc(Nc3ccc4[nH]ncc4c3)c3ccccc3n2)c1]

Belumosudil and processes for making the compound are described in the following US patents: U.S. Pat. Nos. 8,357,693, 9,815,820, 10,183,931, and 10,696,660.

By controlling ROCK2 activity, belumosudil mediates signaling in immune cellular function and fibrotic pathways, thereby alleviating the effects caused by this debilitating disease, such as inflammation of multiple tissues and fibrotic changes that may involve several organs including the lungs, hepatobiliary system, musculoskeletal system, gastrointestinal (GI) tract, and skin.

In vitro assessments have suggested that metabolism of belumosudil is primarily dependent on cytochrome P450 CYP3A4 activity and that the solubility of belumosudil is pH dependent. Preclinical investigations in mouse, rat, rabbit, and dog have indicated that belumosudil undergoes hepatic metabolism to form 2 main metabolites called KD025m1 (a minor metabolite) and KD025m2 (a major metabolite).

KD025m1 has the chemical name 2-(3-(4-(1H-indazol-5-ylamino)quinazolin-2-yl)phenoxy)acetamide, and the following structure:

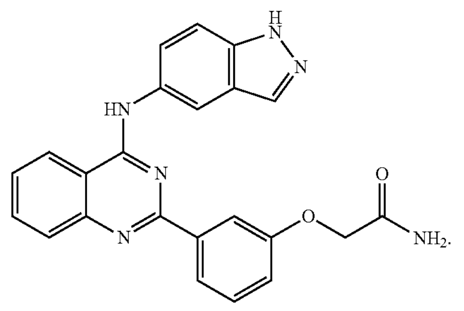 [SMILES: NC(=O)COc1cccc(-c2nc(Nc3ccc4[nH]ncc4c3)c3ccccc3n2)c1]

KD025m2 has the chemical name 2-(3-(4-(1H-indazol-5-ylamino)quinazolin-2-yl)phenoxy)acetic acid, and the following structure:

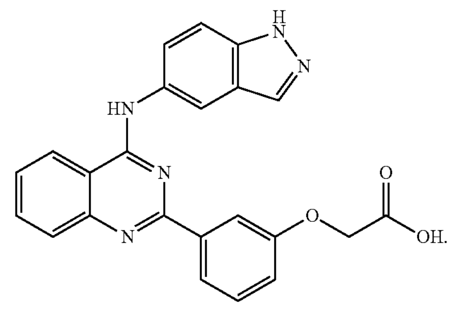 [SMILES: O=C(O)COc1cccc(-c2nc(Nc3ccc4[nH]ncc4c3)c3ccccc3n2)c1]

KD025m1 and KD025m2 were quantified in clinical trials across the belumosudil development program; exposure of the major metabolite KD025m2 was 15% to 20% of the parent, while the minor, more active metabolite KD025m1 had an exposure value <5% of the parent.

Human mass balance studies, using radiolabeled compounds, are important in understanding the pharmacokinetic (PK) properties of an investigational or clinical drug. Mass balance studies are performed to identify and quantify metabolites and determine characteristics of the elimination pathways. One approach for determining absolute bioavailability is use of a microtracer dose.

Understanding the metabolic pathway of an investigational or clinical drug is important in ascertaining the effects of the molecule on the patient, including the energy expended and produced via the metabolic pathways and the molecules synthesized and by-products produced. Understanding the metabolic pathway also is informative as to the enzymes involved in catalyzing the biological mechanisms. The metabolic pathway may thus prove useful in, among other things, determining drug-drug interactions (DDIs), in developing dose modifications, and/or in addressing potential side effects from the drug administration. See, e.g., Schueller, O., Et Al., "*A Phase I Pharmacokinetic Drug Interaction Study of Belumosudil Coadministered With CYP3A4 Inhibitors and Inducers and Proton Pump Inhibitors*," Clinical Pharmacology in Drug Development, 2022, 11(7) 795-806 (use of metabolite exposures in assessing drug-drug interactions).

The present disclosure provides the metabolic pathway for belumosudil. Previously unknown metabolites were identified including the O-dealkylated belumosudil sulfate and belumosudil glucuronide metabolites (identified in plasma), and the monohydroxy-belumosudil, and belumosudil diol metabolites (identified in feces). These compounds may also be useful in the treatment of ROCK2 mediated diseases including cGVHD and/or in developing treatments including treatments for cGVHD such as, for example, in determining DDIs, dose modifications, and addressing side effects.

Definitions

"About" as used herein includes the exact amount modified by the term, about, as well as an amount that would be expected to be within experimental error, such as for example, within 15%, 10%, or 5%. For example, "about 200 mg" means "200 mg" and also a range of mgs that is within experimental error, e.g., plus or minus 15%, 10%, or 5% of 200 mg. As used herein, the term "about" may be used to modify a range and also, a particular value.

"API" means "active pharmaceutical ingredient."

"Allogeneic hematopoietic stem cell transplantation (allo-HSCT)" also called bone marrow transplantation or stem cell transplantation, or "allogeneic hematopoietic cell transplantation (allo-HCT)" refers to a procedure where hematopoietic cells from a donor are grafted into a recipient who is not an identical twin. The source of hematopoietic stem cells for allogeneic transplantation may be peripheral blood stem cells (PBSC) or bone marrow (BM). In some circumstances umbilical cord blood may be used. The donor and recipient may be matched at the human leukocyte antigen (HLA) genes, such as siblings. The donor and recipient may be a parent and a child who are only half-matched (haploidentical).

When the term "belumosudil" is used herein, it should be understood that, unless the context clearly indicates otherwise, the term may cover the compound belumosudil in any form as well as pharmaceutically acceptable salts thereof. The term "belumosudil" refers both to the compound belumosudil (for example, in the free base form, amorphous form, or crystalline form), to pharmaceutically acceptable salts of belumosudil, for example, the mesylate salt form as used in as REZUROCK,™ and to any form of belumosudil that may be used in a formulation or pharmaceutical composition for administering the compound to a patient.

"Clinical endpoint" or "study endpoint" refers to an event or outcome in a clinical trial that can be measured objectively to determine outcomes and potential beneficial effects of the drug or administration protocol as designed in the clinical trial. Examples of clinical endpoints include the following. Overall response rate (ORR) is the percentage of people in a study or treatment group who have a partial response (PR) or complete response (CR) to the treatment within a certain period of time. Failure-free survival (FFS) means the time from the first dose of belumosudil to a failure event, or the interval between the start of belumosudil and the addition of a new cGVHD therapy, relapse of the underlying disease, or nonrelapse mortality (NRM). Overall survival (OS) means the length of time from either the date of diagnosis or the start of treatment for a disease. Duration of response (DOR) means from the time of initial response (e.g., PR or CR) until documented progression from best response of cGVHD, time from initial response to start of additional systemic cGVHD therapy, or death. Time to next treatment (TTNT) means time to initiation of a subsequent systemic cGVHD therapy.

"Clinically recommended amount" or "clinically recommended dosage" refers to the amount or dosage of API that has been recommended and/or approved for administration to a patient by those skilled in the field of medicinal chemistry to treat the disease state in question following clinical trials, for example, as described in Examples 1 and 2 hereof.

"CYP3A" refers to the CYP3A family of p-450 isoenzymes including CYP3A4.

"Disorder" and "disease" are used herein interchangeably, and synonymously, to include within the full scope of either term any condition of a subject in need of treatment.

"Glucuronide" also known as glucuronoside, is any substance produced by linking glucuronic acid to another substance via a glycosidic bond. The glucuronides belong to the glycosides.

"Glucuronidation" refers to the conversion of chemical compounds to glucuronides. It is a method that animals use to assist in the excretion of toxic substances, drugs or other substances that cannot be used as an energy source. Glucuronidation involves the metabolism of parent compound by UDP-glucuronosyltransferases (UGTs) into hydrophilic and negatively charged glucuronides that cannot exit the cell without the aid of efflux transporters. Elimination of the parent compound via glucuronidation in a metabolic active cell is controlled by two driving forces: the formation of glucuronides by UGT enzymes and the (polarized) excretion of these glucuronides by efflux transporters located on the cell surfaces in various drug disposition organs.

"Immunosuppressive therapy" (IST) refers to therapy that is typically administered for at least six months after allo-HSCT to try to prevent GVHD. Examples of IST's include sirolimus, prednisone and calcineurin inhibitors such as tacrolimus and cyclosporine.

"Isolated" as used herein is synonymous with "substantially isolated." "Substantially isolated" as used herein means that the compound has been separated from the in vivo environment in which it was formed via metabolic pathways. For example, when a compound has been formed through the metabolic pathway of a human, the compound is "isolated" when it is no longer contained within the organs or systems of the human body but has been eliminated, excreted ex vivo, and/or otherwise removed from the body, for example, via withdrawal of blood samples containing the compound. "Substantially isolated" includes both partial separation and substantial separation from components of the metabolic pathway. For example, partial separation may include a composition or matter enriched in the compound(s) disclosed herein, for example, containing at least about 5%, and in some embodiments, about 10%, or at least about 15%, by weight of the metabolite. "Substantially separated" can include compositions containing at least about 50%, at least about 60%, at least about 70%, at least about 80%, at least about 90%, at least about 95%, at least about 97%, or at least about 99% by weight of the metabolite.

Lee Symptom Scale (LSS) summary score measures the effect on patients' functioning and well-being. The Lee Symptom Scale is a 30-item scale developed to measure the symptoms of cGVHD and is described in Lee S J, et al., *Development and validation of a scale to measure symptoms of chronic graft-versus host disease*. Biol Blood Marrow Transplant 2002; 8:444-452.

"Line of treatment" or "line of therapy" describes the sequence or order in which different therapies are given to a patient as the patient's disease progresses. Initial treatment (first-line therapy) may not work or may stop working after a period. After first-line therapy is discontinued, a second different treatment (second-line therapy) may be given. Subsequent lines of therapy may be given when a second-line therapy does not work or stops working. Some patients may be administered multiple lines of therapy over the course of a disease.

First-line therapy for National Institutes of Health (NIH)-defined moderate to severe chronic graft-versus-host disease (cGVHD) may be corticosteroids alone or in combination with sirolimus or a calcineurin inhibitor. (Carpenter P A, et al.: *A phase II/III randomized, multicenter trial of prednisone sirolimus versus prednisone sirolimus calcineurin inhibitor for the treatment of chronic graft-versus-host disease*: BMT CTN 0801. Haematologica 103:1915-1924, 2018).

Examples of corticosteroid therapies for treatment of cGVHD include, but are not limited to, prednisone, prednisolone, methylprednisolone, and budesonide. Examples of prior systemic therapies for treating cGVHD include, but are not limited to, prednisone, tacrolimus, extracorporeal photopheresis (ECP), sirolimus, ibruitinib, ruxolitinib, mycophenolate mofetil (MMF), rituximab, methotrexate (MTX), cyclosporine, imatinib, ixazomib, and ofatumumab.

"Metabolic pathway" refers to biochemical reactions for converting (transmuting) one chemical species into another, such as anabolic or catabolic pathways. Anabolic pathways involve constructing a larger molecule from smaller molecules, a process requiring energy. Catabolic pathways involve breaking down of larger molecules, often releasing energy.

"Metabolite" refers to an intermediate or product produced during a metabolic pathway including those produced via anabolic pathways (larger molecule via catabolic pathways (smaller molecules or moieties).

"Myeloablative transplant" refers to a transplantation process using very high doses of chemotherapy or radiation prior to transplantation with autologous or allogeneic hematopoietic stem cells. A non-myeloablative transplant, or reduced intensity transplant, involves the patient having less intensive chemotherapy before transplantation with allogeneic hematopoietic stem cells.

"NIH lung symptom score" or "NIH cGVHD lung score" is a clinical symptom-based score ranging from 0 to 3. A Score 0 is used for no symptoms, Score 1 is used for symptoms of shortness of breath with stairs, Score 2 is used for symptoms of shortness of breath on flat ground, and Score 3 is used for shortness of breath at rest or requiring oxygen.

"Or" is used in the inclusive sense (equivalent to "and/or") unless the context requires otherwise.

"Patient" or "subject" as used herein includes an animal or a human, in one embodiment, a human.

"Pharmaceutical composition" means a mixture of substances suitable for administering to an individual that includes a pharmaceutical agent. For example, a pharmaceutical composition may comprise a sterile aqueous solution or the API formulated in an oral dosage form such as a tablet or capsule.

"Pharmaceutically acceptable salt" means a physiologically and pharmaceutically acceptable salt of a compound provided herein. A "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

"Protocol" as used herein refers to the methods or plan that is used to administer one or more APIs to a subject in need of treatment. The term "protocol" is intended to encompass the overall, detailed plan of care for a patient, as well as individual or partial steps that are part of the overall plan. For example, a protocol may include the dosages used for each API the patient will be (or is) receiving, the combination of APIs the patient receives, the timing and method of administration of each API (for example, considering DDIs, food effects, and impact different formulations or modes of delivery may have on absorption and bioavailability), and management of side effects, as well as the overall plan encompassing the dosages, combinations, timing and methods of administration, and side effects, considered together.

"Side effect" means a physiological response attributable to a treatment other than desired effects. In certain embodiments, side effects include, without limitation, liver function test abnormalities, kidney function abnormalities, liver toxicity, renal toxicity, and myopathies. Side effects may be detected directly or indirectly. For example, increased aminotransferase levels in serum may indicate liver toxicity or liver function abnormality. As another example, increased bilirubin may indicate liver toxicity or liver function abnormality.

"Steroid-refractory" (SR) cGVHD is defined as cGVHD progression while on steroids or corticosteroids; in one embodiment, while on prednisone.

A "therapeutically effective amount" of an API means an amount which, when administered to a human for treating a disease (for example, cGVHD), is sufficient to effect treatment for the disease state being treated. As applied to cGVHD in a human, "treating" or "treatment" includes (1) reducing the risk of developing cGVHD and/or inhibiting cGVHD, i.e., arresting or reducing the development of cGVHD or its clinical symptoms; and (2) relieving cGVHD, i.e., causing regression, reversal, or amelioration of the cGVHD or reducing the number, frequency, duration or severity of its clinical symptoms.

The therapeutically effective amount of an API may vary depending upon the health and physical condition of the subject to be treated, the extent of disease progression, the assessment of the medical situation, and other relevant factors. It is expected that the therapeutically effective amount may fall within a range that can be determined through trial and through reference to clinical trial data and results, for example, as described in Examples 1 and 2 hereof and in scientific literature.

Exemplary Embodiments

The present disclosure provides metabolites of belumosudil and/or the belumosudil metabolic pathway.

In some embodiments, the present disclosure provides an isolated or synthesized compound comprising belumosudil glucuronide, O-dealkylated belumosudil sulfate, monohydroxy belumosudil, and/or belumosudil diol, or a pharmaceutically-acceptable salt thereof.

The compounds and metabolic pathway provided by the present disclosure are useful in the treatment of ROCK2 mediated diseases in patients including in the treatment of autoimmune disorders such as chronic GVHD (cGVHD), and/or in the development of treatment(s) and/or protocols for use in treating ROCK2 mediated diseases.

In one embodiment, the present disclosure comprises use of the compound 2-(3-(4-(1H-indazol-5-ylamino)quinazolin-2-yl)phenoxy)acetamide to treat autoimmune disorders, in some embodiments, to treat cGVHD.

In some embodiments, the present disclosure provides a compound comprising 2-(3-(4-(1H-indazol-5-ylamino)quinazolin-2-yl)phenoxy)acetamide for use in treating an autoimmune disorder in a subject wherein the autoimmune disorder is cGVHD, acute GVHD (aGVHD), pulmonary fibrosis, idiopathic pulmonary fibrosis, moderate to severe psoriasis, rheumatoid arthritis, multiple sclerosis, systemic lupus erythematosus (SLE), Crohn's disease, atopic dermatitis or eczema.

In some embodiments, the present disclosure provides metabolites of belumosudil and/or the belumosudil metabolic pathway for use in preparing a medicament for the treatment of an autoimmune disease in a subject; in some embodiments, for use in preparing a protocol for the treatment of an autoimmune disease in a subject.

In some embodiments, the present disclosure provides metabolites of belumosudil and/or the belumosudil metabolic pathway for use in preparing a protocol comprising the development of a unit dosage (e.g., a clinically recommended unit dosage), for administration of an active pharmaceutical agent to a subject; and/or comprising a combination of active pharmaceutical agents to be administered to the subject (e.g., taking into consideration drug-drug interactions); and/or regarding the timing of administration of one or more active pharmaceutical agents to a subject; and/or for use in averting or minimizing one or more side effects arising from the therapeutic use of at least one active pharmaceutical agent to a subject.

In some embodiments, the present disclosure provides a compound having the formula:

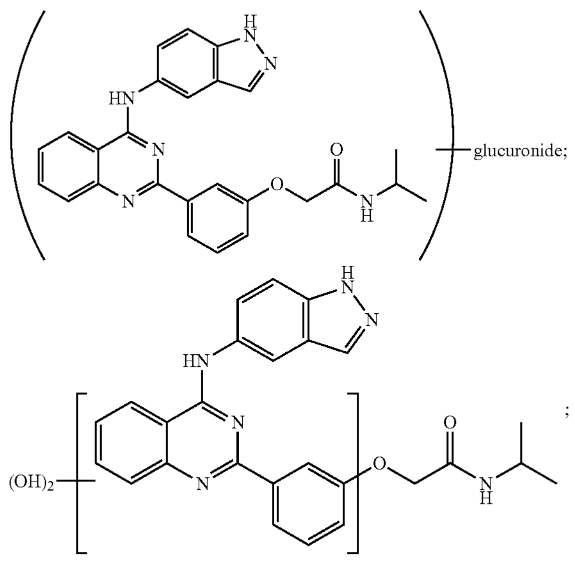

;

-continued

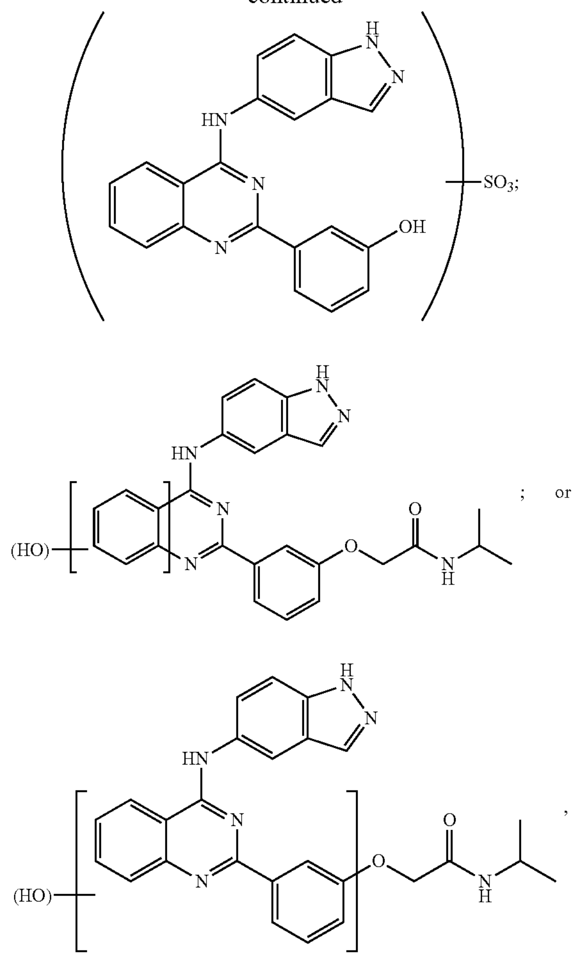

; or

, wherein ______ represents a single bond that links any available carbon atom within the bracketed portion of the molecule to the moiety or moieties adjacent to said brackets; or a pharmaceutically-acceptable salt thereof.

In some embodiments, the disclosure provides an isolated compound that is belumosudil glucuronide having the formula:

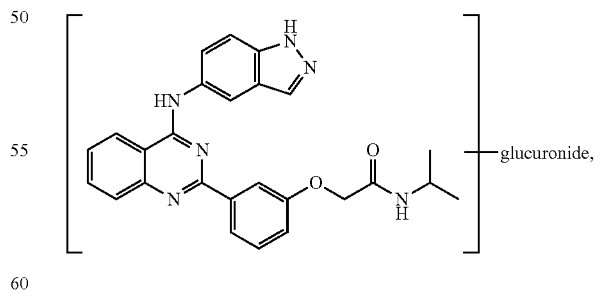

or a pharmaceutically acceptable salt thereof; in some embodiments, wherein the belumosudil glucuronide has a molecular weight of 628.

In some embodiments, the disclosure provides an isolated compound that is O-dealkylated belumosudil sulfate, having the formula:

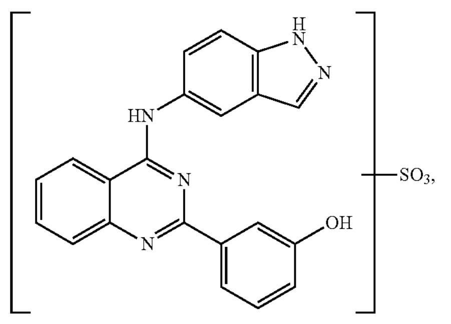

or a pharmaceutically acceptable salt thereof; in some embodiments, wherein the O-dealkylate belumosudil sulfate has a molecular weight of 433.

In some embodiments, the disclosure provides an isolated compound that is monohydroxy belumosudil having the formula:

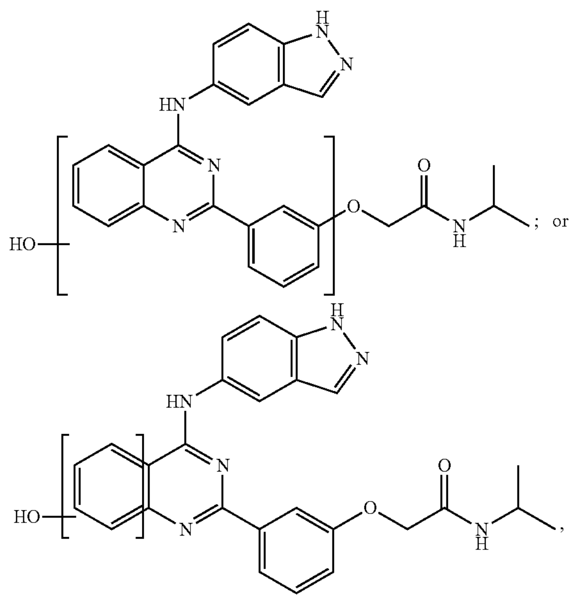

or a pharmaceutically acceptable salt thereof; in some embodiment, wherein the monohydroxy belumosudil has a molecular weight of 468.

In some embodiments, the disclosure provides an isolated compound that is belumosudil diol having the formula:

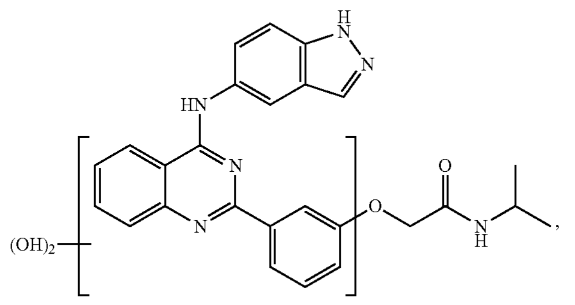

or a pharmaceutically acceptable salt thereof; in some embodiments, wherein the belumosudil diol has a molecular weight of 486.

In some embodiments, the present disclosure provides a pharmaceutical composition comprising any one or more of the aforesaid compounds, or use of said pharmaceutical composition to treat an autoimmune disorder in a subject wherein the autoimmune disorder is chronic GVHD (cGVHD), acute GVHD (aGVHD), pulmonary fibrosis, idiopathic pulmonary fibrosis, moderate to severe psoriasis, rheumatoid arthritis, multiple sclerosis, systemic lupus erythematosus (SLE), Crohn's disease, atopic dermatitis or eczema.

In some embodiments, the present disclosure provides a pharmaceutical composition comprising any one or more of the aforesaid compounds, or use of said pharmaceutical composition to treat an autoimmune disorder.

In some embodiments, the present disclosure provides a pharmaceutical composition comprising any one or more of the aforesaid compounds, or use of said pharmaceutical composition to treat chronic GVHD (cGVHD).

In some embodiments, the present disclosure provides a pharmaceutical composition comprising any one or more of the aforesaid compounds, or use of said pharmaceutical composition to treat acute GVHD (aGVHD).

In some embodiments, the present disclosure provides a pharmaceutical composition comprising any one or more of the aforesaid compounds, or use of said pharmaceutical composition to treat pulmonary fibrosis.

In some embodiments, the present disclosure provides a pharmaceutical composition comprising any one or more of the aforesaid compounds, or use of said pharmaceutical composition to treat idiopathic pulmonary fibrosis.

In some embodiments, the present disclosure provides a pharmaceutical composition comprising any one or more of the aforesaid compounds, or use of said pharmaceutical composition to treat moderate to severe psoriasis.

In some embodiments, the present disclosure provides a pharmaceutical composition comprising any one or more of the aforesaid compounds, or use of said pharmaceutical composition to treat multiple sclerosis.

In some embodiments, the present disclosure provides a pharmaceutical composition comprising any one or more of the aforesaid compounds, or use of said pharmaceutical composition to treat systemic lupus erythematosus (SLE).

In some embodiments, the present disclosure provides a pharmaceutical composition comprising any one or more of the aforesaid compounds, or use of said pharmaceutical composition to treat Crohn's disease.

In some embodiments, the present disclosure provides a pharmaceutical composition comprising any one or more of the aforesaid compounds, or use of said pharmaceutical composition to treat atopic dermatitis.

In some embodiments, the present disclosure provides a pharmaceutical composition comprising any one or more of the aforesaid compounds, or use of said pharmaceutical composition to treat eczema.

In some embodiments, the subject receiving said treatment has had allogeneic hematopoietic stem cell transplantation that is a matched-HSCT. In some embodiments, the allogeneic hematopoietic stem cell transplantation is a haploidentical-HSCT.

In some embodiments, belumosudil treatment is continued based on the patient's tolerability until active cGVHD symptoms resolve or progress. The number of cycles and duration of the treatment is patient dependent. In some embodiments, the belumosudil is administered to the patient in one or more 28-day cycles.

In some embodiments, the number of cycles ranges from 3 to 15. In some embodiments, the number of cycles ranges from 3 to 14, from 3 to 13, from 3 to 12, from 3 to 11, from 3 to 10, from 3 to 9, from 3 to 8, from 3 to 7, from 3 to 6, from 3 to 5, or from 3 to 4. In some embodiments, the number of cycles ranges from 5 to 11. In some embodiments, the number of cycles ranges from 6 to 12. In some embodiments, the number of cycles ranges from 5 to 10, from 5 to 9, or from 5 to 8. In some embodiments, the number of cycles ranges from 5 to 7. In some embodiments, the number of cycles ranges from 5 to 6. In some embodiments, the number of cycles is 5. In some embodiments, the number of cycles is 6. In some embodiments, the number of cycles is 7. In some embodiments, the number of cycles is 3, 4, 5, 6, 7, 8, 9, 10, 11, 12, 13, 14, or 15.

In some embodiments, the number of cycles ranges from 3 cycles to loss of response. In some embodiments, the number of cycles ranges from 4 cycles to loss of response. In some embodiments, the number of cycles ranges from 5 cycles to loss of response. In some embodiments, the number of cycles ranges from 6 cycles to loss of response. In some embodiments, the number of cycles ranges from 7 cycles to loss of response. In some embodiments, the number of cycles ranges from 8 cycles to loss of response. In some embodiments, the number of cycles is greater than 3, 4, 5, 10, 15, 20, 25, or 30, or until a desired response is achieved.

In some embodiments, the subject experiences an improvement as defined by the Lee Symptom Scale (LSS). In some embodiments, the subject experiences at least a 7-point reduction in the LSS score. In some embodiments, the subject experiences at least a 10-point reduction in the LSS score. In some embodiments, the improvement is maintained over at least two consecutive evaluations. In some embodiments the LSS score is evaluated at baseline and on day 1 of each cycle starting at cycle 2 day 1.

In some embodiments, the subject has chronic graft-versus-host disease and has failed one to three prior lines of systemic therapy for the chronic graft-versus-host disease. In some embodiments, the subject has chronic graft-versus-host disease and has failed at least two prior lines of systemic therapy for the chronic graft-versus-host disease. In some embodiments, the subject has chronic graft-versus-host disease and has failed two to five prior lines of systemic therapy for the chronic graft-versus-host disease. In some embodiments, the subject has failed at least one, at least two, at least three, at least four, or at least five prior lines of systemic therapy for the chronic graft-versus-host disease.

In some embodiments, the subject experienced a complete response to last treatment for the graft-versus-host disease prior to belumosudil. In some embodiments, the subject experienced a partial response to last treatment for the graft-versus-host disease prior to belumosudil. In some embodiments, stable disease during the last treatment for the graft-versus-host disease prior to belumosudil.

In some embodiments, the prior lines of systemic therapy for the chronic graft-versus-host disease have been discontinued.

In some embodiments, the prior lines of systemic therapy are selected from the group consisting of prednisone, tacrolimus, ECP, sirolimus, ibruitinib, ruxolitinib, MMF, rituximab, MTX, cyclosporine, imatinib, ixazomib, and ofatumumab.

In some embodiments, the cGVHD is steroid-refractory (SR) cGVHD. In some embodiments, the subject is refractory to the last line of treatment prior to belumosudil treatment.

In some embodiments, the subject is receiving concomitant corticosteroid therapy. In some embodiments, the concomitant corticosteroid therapy is selected from the group consisting of prednisone, prednisolone, methylprednisolone, and budesonide. In some embodiments, the concomitant corticosteroid therapy is prednisone. In some embodiments, the dose of the concomitant corticosteroid therapy is reduced after at least 1 cycle of the belumosudil treatment. In some embodiments, the dose of the concomitant corticosteroid therapy is reduced by at least about 10%, by at least about 20%, by at least about 30%, by at least about 40%, by at least about 50%, by at least about 60%, or by at least about 70% after at least 1 cycle of the belumosudil treatment. In some embodiments, the dose of the concomitant corticosteroid therapy is reduced by from about 10% to about 70%, from about 15% to about 65%, from about 20% to about 60%, from about 30% to about 60%, from about 35% to about 60%, from about 40% to about 60%, or from about 45% to about 55% after at least 1 cycle of the belumosudil treatment. In some embodiments, the concomitant corticosteroid therapy is discontinued after at least 1 cycle of the belumosudil treatment.

In some embodiments, the subject is receiving concomitant calcineurin inhibitor therapy.

In some embodiments, the subject has involvement of at least 4 organs. In some embodiments, the subject has involvement of at least 3 organs. In some embodiments, the subject has involvement of at least 2 organs.

Compositions and Tablets

According to another aspect, pharmaceutical compositions are disclosed that include a compound described herein as an active ingredient. These pharmaceutical compositions comprise an effective dose of at least one compound disclosed herein, or a pharmaceutically acceptable salt of the said compound, and also at least one pharmaceutically acceptable excipient.

The said excipients are selected, in accordance with the pharmaceutical form and method of administration desired, from the customary excipients, which are known to a person skilled in the art.

In these pharmaceutical compositions for oral, parenteral (including subcutaneous, intramuscular, intradermal and intravenous), transdermal, bronchial or nasal administration, the active ingredient of formula (I) above, or its salt, may be administered in a unit administration form, in a mixture with conventional pharmaceutical excipients, to animals and to human beings for the prophylaxis or treatment of the below disorders or diseases.

Pharmaceutical compositions described herein and/or for use in the methods described herein may further comprise a pharmaceutically acceptable carrier/excipient. In some embodiments, the pharmaceutically acceptable carrier means a pharmaceutically-acceptable substrate, material, composition or vehicle to aid in the process of delivery of the API to the patient, and/or to stabilize the API during transport for delivery to the patient, such as a diluent, solid filler, excipient, or manufacturing aid (e.g., lubricant, talc, magnesium, calcium or zinc stearate, or steric acid). The term "acceptable" as used in this sense means that the material is compatible with the other ingredients of the formulation and does not produce intolerable side effects injurious to the patient.

Pharmaceutical compositions contemplated herein include suitable dosage forms for oral, parenteral (including subcutaneous, intramuscular, intradermal and intravenous), transdermal, bronchial or nasal administration.

In solid pharmaceutical dosage forms for oral administration (capsules, tablets, pills, powders, granules, and the like), the API may be mixed with at least a pharmaceutically-acceptable carrier including one or more pharmaceutically-acceptable excipients.

In one embodiment, the compounds are formulated into a tablet for oral administration. Belumosudil mesylate is a yellow powder that is practically insoluble in water. Belumosudil tablets may be prepared for oral administration. Each tablet contains 200 mg of the free base equivalent to 242.5 mg of belumosudil mesylate. The tablet also may contain the following inactive ingredients: microcrystalline cellulose, hypromellose, croscarmellose sodium, colloidal silicon dioxide, and magnesium stearate. The tablet film consists of polyvinyl alcohol, polyethylene glycol, talc, titanium dioxide and yellow iron oxide. Each 200 mg tablet is a pale-yellow film-coated oblong tablet debossed with "KDM" on one side and "200" on the other side. Tablets are stored at room temperature, 20° ° C. to 25° C. (68° F. to 77° F.); excursions permitted from 15° C. and 30° ° C. (59° F. to 86° F.).

The compounds and pharmaceutical compositions disclosed herein may be useful for inhibiting ROCK1 and/or ROCK2 enzymes, preferentially ROCK2, and therefore may be useful in treating diseases regulated by ROCK enzymes such as autoimmune disorders and/or fibrotic disorders including GVHD (chronic and acute), pulmonary fibrosis, idiopathic pulmonary fibrosis, moderate to severe psoriasis, rheumatoid arthritis, multiple sclerosis, systemic lupus erythematosus (SLE), Crohn's disease, dermatitis (e.g., atopic dermatitis), and eczema, among other indications.

The following abbreviations may be helpful in considering the Examples and description herein.

| Abbreviations | |
|---|---|
| AE | Adverse events |
| AMS | Accelerator mass spectrometry |
| alloHCT | allogeneic hematopoietic cell transplantation |
| BID | Twice daily (bi-daily) |
| BM | Bone marrow |
| cGVHD | Chronic graft versus host disease |
| CMV | cytomegalovirus |
| CR | Complete response |
| DDI | Drug-drug interaction |
| DOR | Duration of response |
| EOI | End of infusion |
| FFS | Failure-free survival |
| HLA | human leukocyte antigen |
| IST | Immunosuppressive therapy |
| IV | Intravenous |
| LSC | Liquid scintillation counting |
| LSS | Lee Symptom Scale |
| NMT | Not more than |
| ORR | Overall response rate |
| OS | Overall survival |
| PBSC | peripheral blood stem cells |
| PPI | Proton pump inhibitors |
| PR | Partial response |
| QOL | Quality of life |
| SD | Standard deviation |
| SR | Steroid refractory |
| TEAEs | treatment-emergent adverse events |
| TTNT | Time to next treatment |
| QD | Daily; every day |

EXAMPLES

Example 1: A Phase I, Open-Label, 2-Part Study on Absolute Bioavailability, Mass Balance, and Metabolic Profiling Assessment of [$^{14}$C]-Belumosudil in Healthy Subjects In this phase 1 two-part study, the pharmacokinetics, mass balance, and metabolic profile of belumosudil were evaluated after subjects were administered single doses of unlabeled belumosudil oral tablets (200 mg), radiolabeled belumosudil intravenous (IV) microtracer infusions (100 μg), and radiolabeled oral capsules (200 mg). The study was conducted in 2 parts with the following objectives: (1) to determine absolute oral bioavailability of belumosudil (part 1), (2) to determine mass balance recovery after a single oral dose of radiolabeled belumosudil (part 2), and (3) to conduct metabolite profiling and structural elucidation of identified metabolites (part 2).

Absolute bioavailability based on area under the plasma concentration-time curve from time 0 to infinity for the oral dose/area under the plasma concentration-time curve from time 0 to infinity for the IV dose was calculated as 63.7%. Radiolabeled IV microtracer dosing demonstrated a low extraction ratio and distribution of belumosudil into tissues. The majority of total radioactivity was recovered in feces, with minimal amounts recovered in urine, suggesting minimal renal elimination of belumosudil.

Study Design

This was a single-center, nonrandomized, open-label, 2-part study in 5 healthy male subjects aged 30 to 65 years. All oral doses were administered following an overnight fast and a standard breakfast on the day of dosing.

For the absolute bioavailability evaluation (part 1), subjects were administered a single oral dose of a 200-mg belumosudil tablet (therapeutic dose) followed 1.75 hours later by a 15-minute IV infusion of 100 μg [$^{14}$C]-belumosudil containing not more than (NMT) 37 kBq [$^{14}$C] (timed to occur at the expected maximum concentration [Cmax]). To determine absolute bioavailability, a microtracer dose was chosen as it negates the need for an IV formulation with good stability. Additionally, due to use of a very low dose, further nonclinical studies such as local tolerance and general toxicology studies were not warranted.

For the mass balance and metabolic profiling study (part 2), following at least a 7-day washout from part 1, subjects received a single oral dose of a 200 mg [$^{14}$C]-belumosudil capsule containing NMT 9.8 MBq [$^{14}$C]. This level of radioactivity was selected based on human dosimetry calculations conducted by Public Health England that determined a radioactive oral dose of NMT 9.8 MBq would be necessary to permit adequate metabolite profiling of key samples. Taking the part 1 microtracer dose into account, the total committed effective dose subjects received in the study was 3 mSv, which falls within the International Commission on Radiological Protection Guidelines for Category IIb studies. Additionally, to remain within the limit for radioactive dose approved by the UK Administration of Radioactive Substances Advisory Committee, the target-specific activity of [$^{14}$C]-belumosudil was set to 90% of the threshold radioactive dosing limit.

Pharmacokinetic Sample Collection and Analysis

Part 1 Blood Sampling.

Blood samples for oral belumosudil PK analysis were collected in tripotassium ethylenediaminetetraacetic acid tubes before dosing and 0.5, 1, 1.5, 2, 3, 4, 5, 6, 8, 10, 12, 24, 36, and 48 hours after dosing. Blood samples for IV [$^{14}$C]-belumosudil PK analysis and total radioactivity were collected at −0.25, −0.16, −0.08, 0, 0.08, 0.16, 0.25, 0.5, 0.75, 1, 1.5, 2, 3, 4, 5, 6, 8, 10, 12, 22, 34, and 46 hours after the end of infusion (EOI). All samples were processed to plasma within 30 minutes of collection by centrifugation at 2000 g for 10 minutes at 4° C., and then frozen at −70° C. or below prior to analysis.

Part 2 Blood Sampling.

Whole-blood samples for total radioactivity and plasma samples for metabolite pro-filing and identification were collected before dosing and 1, 4, 8, 12, 24, 48, 72, 96, 120, 144, and 168 hours after dosing. Blood samples for plasma belumosudil, KD025m1, KD025m2, and total radioactivity analysis were collected at the same time points, with additional samples collected 0.5, 1.5, 2, 3, 5, 6, 8, 10, and 36 hours after dosing. Whole-blood samples for total radioactivity were collected into tripotassium ethylene-diaminetetraacetic acid tubes and stored at 2 to 8° C. pending analysis. Blood samples for plasma belumosudil, KD025m1, KD025m2, and total radioactivity quantification and metabolite profiling/identification were processed similarly to part 1 and stored frozen at −20° C. (belumosudil, KD025m1, KD025m2, and total radioactivity samples) or −70° ° C. (metabolite profiling samples).

Part 2 Urine and Feces Sampling.

Urine for total radioactivity and metabolite profiling and identification was collected before dosing (the first void of the day) and pooled from 0 to 6, 6 to 12, and 12 to 24 hours after dosing followed by daily (24-hour) collections until day 8/discharge. Urine samples were pooled per interval and stored at 2 to 8° C. pending analysis. Feces were collected from admission until before dosing and then daily (24-hour) collections until discharge. Fecal samples were pooled per time interval and stored at −20° C. pending analysis.

Analytical Methods

Part 1. Belumosudil plasma samples were prepared for analysis using a protein precipitation method and were quantified using a validated liquid chromatography-tandem mass spectrometry (LC-MS/MS) method with a lower limit of quantitation (LLOQ) of 10 ng/mL.

Total [$^{14}$C]-belumosudil concentrations were determined by accelerator mass spectrometry (AMS). Prior to AMS analysis, selected samples were analyzed by liquid scintillation counting (LSC) to ensure that radioactivity levels did not saturate the AMS. Selected samples were diluted with commercial plasma to ensure that concentrations would fall within the accept-able range for AMS analysis. The samples were converted to graphite through combustion to $CO_2$ followed by reduction to graphite. The graphite targets were then analyzed by AMS (LLOQ of 0.00489, 0.00557, 0.00485, 0.00402, and 0.00372 ng equiv/mL for individual subjects). All $^{14}$C data was background-corrected based on predose [$^{14}$C]-belumosudil concentrations.

[$^{14}$C]-belumosudil concentrations were quantified by a high-performance liquid chromatography with accelerator mass spectrometry (HPLC AMS) method.[19] Radiolabeled belumosudil in plasma was prepared for sample analysis using a protein precipitation method, and HPLC was subsequently performed. Eluate fractions corresponding to [$^{14}$C]-belumosudil were collected before AMS analysis (LLOQ of 1.55 pg equiv/mL).

Part 2. Belumosudil, KD025m1, and KD025m2 plasma concentrations were quantified by LC-MS/MS as in part 1

Total radioactivity whole-blood, plasma, and urine samples were prepared for LSC by mixing with scintillation fluid. In addition, aliquots of whole blood were solubilized with AquiGest tissue solubilization fluid and plasma samples were mixed with 10 mM of phosphate-buffered saline. Urine and fecal samples were pooled per subject by time interval before analysis. In addition, fecal samples were combusted using an automatic sample oxidizer prior to LSC. Radioactivity in all samples was measured using an LSC with automatic external standard quench correction (2300TR, 2900TR, and 3100TR Tri-Carb, Scintillation Counters; PerkinElmer, Waltham, Massachusetts), with samples counted for 4 minutes. The LLOQ was considered to be twice the background value for samples of the same type (1.39 [urine], 23.9 [feces], 35.5 [whole blood], and 30.9 [plasma] ng equivalents [free base]/g or mL).

To determine the most appropriate sampling pools for metabolite identification/profiling, plasma, urine, and fecal samples were pooled based on mass balance data obtained as described above. Plasma samples were pooled for individual subjects by time points that represented at least 80% of the plasma total radioactivity, as well as pooled across subjects before dosing and at 4-hour and 8-hour time points. Urine samples were pooled from 0 to 24 hours for individual subjects and across subjects for predose and 0- to 6-hour intervals. Fecal samples were pooled for individual subjects depending on time points that represented at least 80% of the plasma total radioactivity and across subjects at 0- to 24- and 24- to 48-hour intervals.

[$^{14}$C]-belumosudil concentrations were quantified by LC-MS/MS. Chemical structures were then identified for those radioactive components that accounted for >10% of circulating radioactivity in plasma and >10% of the dose in urine and feces. Radioactive components that represented <10% of circulating radioactivity in plasma and <10% of the dose in urine and feces were also identified. Metabolite identification was then performed using accurate mass positive and negative ion full scan and positive ion product ion analyses. Samples were screened for the presence of belumosudil, metabolites KD025m1, KD025m2, O-dealkylated belumosudil, any potential metabolites resulting from O-dealkylation and hydroxylation, and phase 2-conjugated metabolites. Any identified components were compared with [$^{14}$C] radiochromatograms to identify the metabolite. Predose plasma and urine pools were used to correct for endogenous components during metabolite identification.

Pharmacokinetic Assessments

PK parameters for plasma total radioactivity, belumosudil, [$^{14}$C]-belumosudil (part 1 only), and KD025m1 and KD025m2 (part 2 only) were calculated using standard noncompartmental methods in Phoenix WinNonlin version 8.0 (Certara, Princeton, New Jersey). PK parameter estimates were used to calculate absolute bioavailability and metabolite-to-parent ratio.

PK parameters calculated for this study were absolute bioavailability of belumosudil (as assessed by dose-adjusted area under the plasma concentration-time curve (AUC) from time 0 to infinity for the oral dose ($AUC_{inf,oral}$)/AUC from time 0 to infinity for the IV dose ($AUC_{inf,IV}$); mass balance recovery of total radioactivity in all excreta (as assessed by amount eliminated [Ae], % Ae, cumulative Ae, and cumulative % Ae); various PK parameters for oral belumosudil, KD025m1, and KD025m2, and total radioactivity; PK parameters for IV [$^{14}$C]-belumosudil; routes and rates of [$^{14}$C] elimination (plasma and excreta); total radioactivity whole blood:plasma ratios; and metabolite structural identification in plasma and excreta.

The PK population included all subjects in either part 1 or 2 who received at least 1 dose of belumosudil and provided enough data for at least 1 PK profile, if they fulfilled the following criteria: (1) no missing samples at critical time points, (2) no protocol deviations that impacted PK end points, and (3) no adverse events (AEs) that suggest the whole dose was not delivered to the subject (e.g., vomiting or infusion site reaction).

The mass balance population included all subjects in part 2 who received at least 1 dose of belumosudil, had evaluable total radioactivity concentrations in urine/fecal samples, and had no protocol deviations that may have affected the mass balance analysis.

Safety Assessments

Safety was assessed throughout the study by AEs, vital signs, electrocardiograms, physical examinations, and clinical laboratory tests. The safety population included all subjects who received at least 1 dose of the study drug (oral or IV) in either part of the study.

Results

Subject Disposition

Five male subjects were enrolled and dosed in both parts 1 and 2. All subjects completed the study and were included in both the PK population and mass balance population. Baseline demographics are summarized in Table 1. Subjects were aged between 41 and 64 years (mean age, 53.0 years), and the majority of subjects were White. All subjects were within the protocol-defined reference range for body mass index.

TABLE 1

| Subject Demographics | |
|---|---|
| Demographic | Mean, SD |
| Age, y | 53.0 (8.7) |
| Height, cm | 172.6 (6.7) |
| Weight, kg | 83.3 (13.3) |
| BMI, kg/$m^2$ | 27.9 (3.1) |
| Demographics | n (%) |
| Sex: Male | 5 (100) |
| Race: White | 4 (80.0) |
| Race: other, Caribbean | 1 (20.0) |

SD, standard deviation

Pharmacokinetic Evaluation

Part 1: Absolute Bioavailability of Belumosudil.

Figure 2:
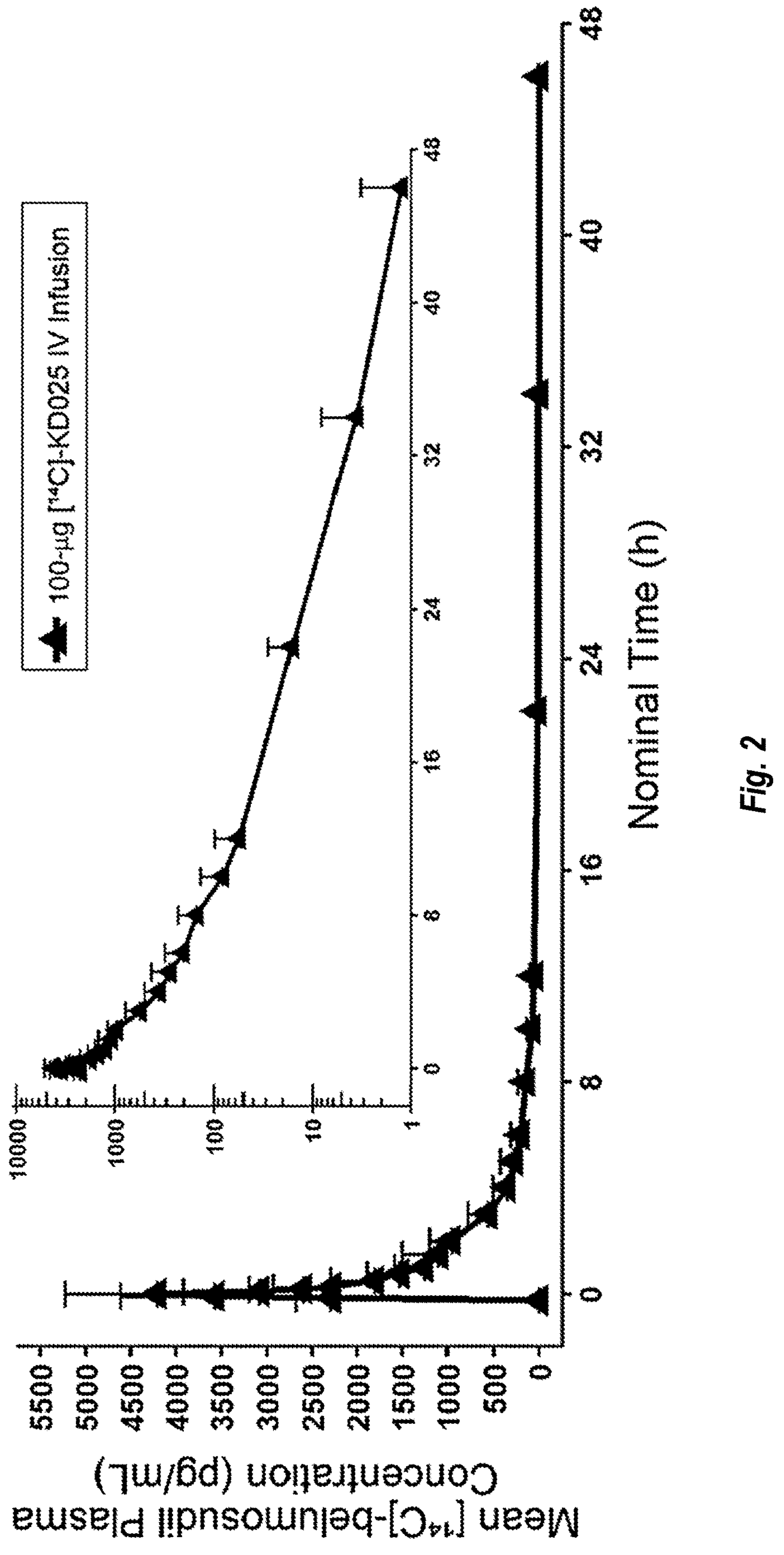
FIG. 2 is a graph showing mean PK profiles for [$^{14}$C]-belumosudil after administration of a single 200-mg dose of belumosudil followed by a 15-minute [$^{14}$C]-belumosudil IV infusion. The inset graph shows the data on a log-linear scale.
Figure 3:
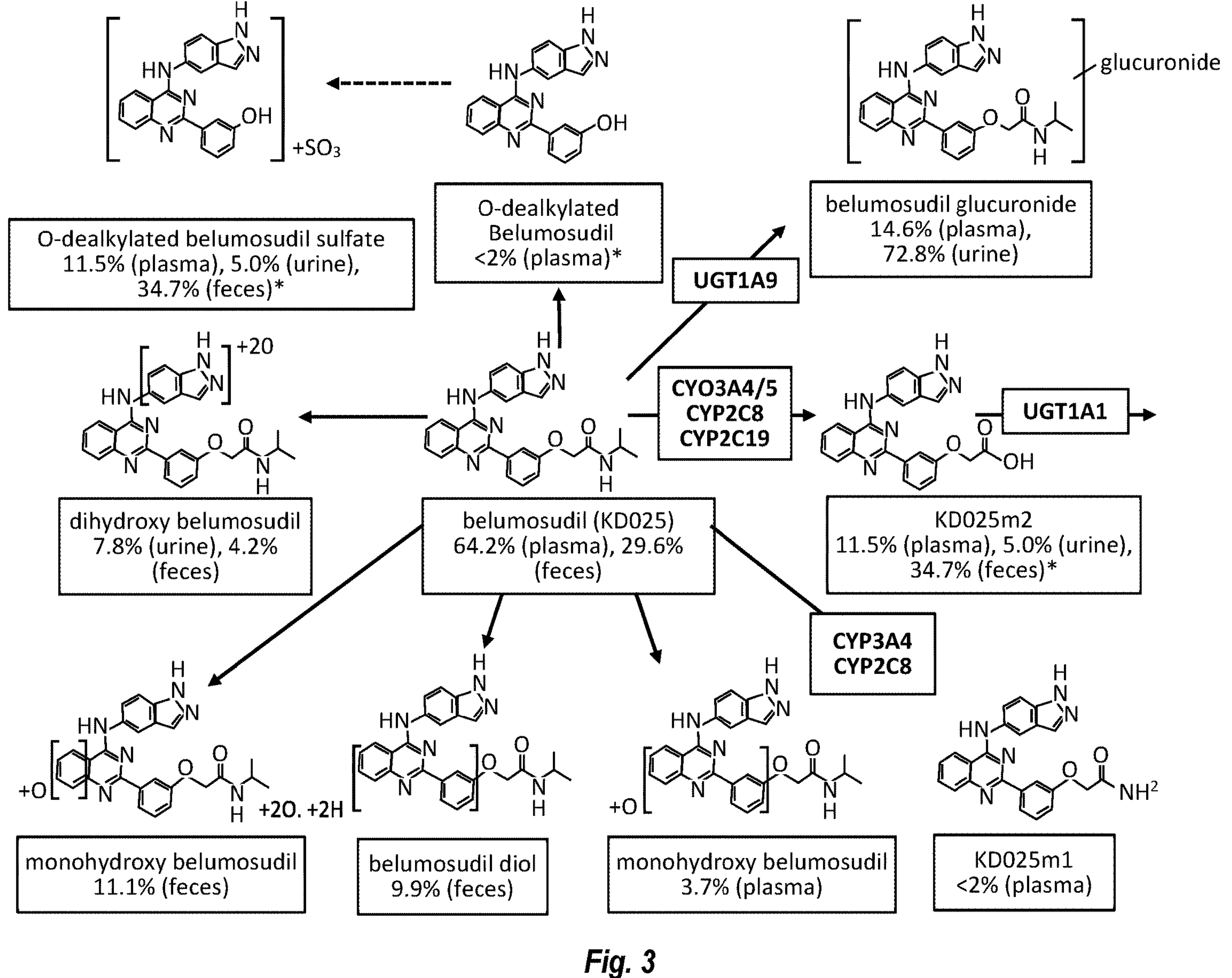
FIG. 3 shows the metabolic pathway for belumosudil in humans.

Mean PK profiles for a single 200-mg oral dose of belumosudil followed by a 15-minute [$^{14}$C]-belumosudil IV infusion are shown in FIG. 2 (unlabeled belumosudil) and FIG. 3 ([$^{14}$C]-belumosudil). PK parameters calculated for belumosudil, [$^{14}$C]-belumosudil, and total radioactivity in part 1 of the study are presented in Table 2.

TABLE 2

Summary of Belumosudil and Total Radioactivity Pharmacokinetics Parameters in Part 1 and Part 2

| | Part 1 (n = 5) | | | Part 2 (n = 5) | |
|---|---|---|---|---|---|
| Parameter, Unit | Belumosudil, 200-mg Tablet | [$^{14}$C]-Belumosudil, 100 µg IV | Total Radioactivity, 100 µg IV | [$^{14}$C]-Belumosudil, 200-mg Capsule | Total Radioactivity, 200-mg Capsule |
| $t_{max}$, h | 2.0 (1.0-4.0) | 0.25 (0.24-0.25) | 0.25 (0.24-0.32) | 2.0 (1.5-2.1) | 2.1 (1.0-4.0) |
| $C_{max}$, ng or ng equiv/mL | 1870 (36.7); 1960 (649) | 4480 (18.0); 4530 (830) | 4.82 (20.0); 4.89 (1.00) | 1680 (32.1); 1740 (472 | 2950 (21.5); 3000 (552) |
| $AUC_{last}$, ng or ng equiv × h/mL | 8120 (41.2); 8730 (4270) | 6440 (29.5); 6680 (2220) | 12.7 (23.7) 13.0 (3.10) | 7850 (39.3); 8270 (2740 | 23600 (35.3); 24 700 (8030) |
| $AUC_{inf}$, ng or ng equiv × h/mL | 8300 (40.2); 8890 (4240) | 6480 (29.3); 6720 (2220) | 13.9 (23.7) 14.2 (3.26) | 8100 (37.0); 8490 (2680) | 28 300 (46.1); 30 000 (11400) |
| $AUC_{extrap}$, % | 1.95 (64.6); 2.18 (0.919) | 0.53 (66.3); 0.63 (0.46) | 8.09 (35.4); 8.48 (2.84) | 2.46 (92.9); 3.08 (2.16) | 9.76 (31.7); 10.1 (2.79) |
| $T_{1/2}$, h | 5.30 (66.7); 6.05 (3.20) | 5.86 (35.8); 6.15 (2.14) | 18.0 (22.6); 18.3 (3.90) | 5.11 (37.9); 5.39 (1.96) | 52.8 (92.0); 62.5 (35.6) |
| Clearanance mL/min[1] | 402 (40.2); 423 (126) | 2.56 (29.3); 264 (64.3) | 120 (23.7); 122 (29.0) | 412 (37.0); 435 (173) | 118 (46.1); 126 (59.7) |
| Volume, L[a] | NR | 130 (38.9); 138 (59.8) | 186 (35.4); 194 (53.2) | NR | NR |
| Volume, ss, L | NA | 53.2 (20.6); 54.1 (10.7) | 98.2 (23.4) | NA | NA |
| F, $C_{max}$, % | 23.7(9.3); 23.8 (2.21) | NA | NA | 62.2 (26.6)[b]; 63.8 (15.7)[b] | NA |
| F, $AUC_{inf}$, % | 63.7 (17.3); 64.5 (10.4) | NA | NA | 62.2 (26.6)[b]; 63.8 (15.7)[b] | NA |

$AUC_{extrap}$, $AUC_{inf}$, area under the plasma concentration-time curve from time 0 to infinity;

$AUC_{last}$, area under the plasma concentration-time curve from time 0 to the last quantifiable concentration;

Cmax, maximum concentration;

F, bioavailability;

NA, not applicable;

NR, not reported;

$t_{1/2}$, half-life;

$t_{max}$, time to maximum concentration.

With the exception of $t_{max}$, all parameters are presented as geometric mean (geometric CV %), arithmetic mean (standard deviation).

$T_{max}$ is presented as median (min-max).

[a]Apparent clearance and volume for belumosudil administered as a table or capsule.

[b]F in part 2 is calculated based on the intravenous [$^{14}$C]-belumosudil dose administrated in part 1 and the oral [$^{14}$C]-belumosudil dose administered in part 2.

For the IV [14C]-belumosudil infusion, maximum radiolabeled concentrations were achieved at the EOI, then declined in a biphasic manner. Radiolabeled concentrations remained quantifiable through the final sampling time point (46 hours post-EOI) and terminal half-lives were calculated for all subjects (geometric mean, 5.9 hours).

Peak belumosudil concentrations following oral administration were reached 3 hours after the oral dose, then declined in a biphasic manner through 48 hours. Terminal half-life was reported for all 5 subjects (geometric mean, 5.3 hours). Absolute bioavailability ($AUC_{inf,oral}/AUC_{inf,IV}$) was calculated as 63.7%.

Part 2: Mass Balance and Excretion.

The majority of radioactivity (88.5%) was recovered in excreta, with 84.6% recovered in the feces and <5% of the radiolabeled dose recovered in the urine. Within the first 24 hours after dosing, ~27.4% and 3.8% of the total radioactivity was recovered in the feces and urine, respectively. Whole blood:plasma total radioactivity concentrations ranged from 0.53 to 1.16. PK parameters for belumosudil and total radioactivity in part 2 are summarized above in Table 2.

Part 2: Metabolite Identification and Profiling.

Structural identification was attempted on radioactive components representing 10% of the circulating radioactivity in plasma and accounting for >10% of the dose in feces. Identified belumosudil metabolites in plasma, urine, and feces are presented in Table 3. No single radioactive component present in urine accounted for >10% of the dose. In plasma, belumosudil accounted for 64% of the total plasma radioactivity; KD025m2 and the previously unidentified phase 2 metabolite O-dealkylated belumosudil sulfate were a combined 11.5% of the total plasma radioactivity. Another metabolite that has not been measured in clinical studies, belumosudil glucuronide, accounted for 15% of the total plasma radioactivity. In feces, belumosudil was 30% and KD025m2 and O-dealkylated belumosudil sulfate accounted for a combined 35% of the total sample radioactivity. The previously unidentified belumosudil diol (belumosudil+2O, +2H) and monohydroxy belumosudil were 10% and 11% in feces, respectively.

TABLE 3

Metabolite Identification in Plasma, Urine and Feces
% ROI

| Metabolite | Molecular Weight, Da[a] | Retention Time, min[b] | Plasma | Urine | Feces |
|---|---|---|---|---|---|
| Dihydroxy belumosudil | 484 | 17.6 | NA | U5 (7.81) | F3 (4.22 |
| O-dealkylated belumosudil sulfate (co-eluting) | 433 | 24.7 | P3 (11.54)[c] | U7 (5.02)[c] | F6 (34.72)[c] |
| KD025 m$^2$ (co-eluting) | 411 | 25.0 | P3 (11.54)[c] | U7 (5.02)[c] | F6 (34.72)[c] |
| Belumosudil glucuronide | 628 | 31.4 | P4 (14.63) | U8 (72.78) | NA |
| Belumosudil diol (belumosudil + 2O, + 2H) | 486 | 41.7 | NA | NA | F7 (9.92) |
| Monohydroxy belumosudil | 468 | 43.4 | NA | NA | F8 (11.14) |
| Belumosudil | 452 | 89.6 | P6 (64.17) | NA | F10 (29.60) |
| Monohydroxy belumosudil | 468 | 93.9 | P7 (3.65) | NA | NA |

NA, Component not present or below threshold required for metabolite identification;
% ROI, Mean % contribution of this region of interest to total sample radioactivity (across subjects).
P, U, and F represent HPLC eluates in plasma, urine, and feces samples, respectively.
Bold indicates > 10% circulating radioactivity in at least 1 plasma sample or > 10% of the dose in at least 1 feces sample.
[a]Molecular weights are monoisotopic and refer to unlabeled components.
[b]Nominal retention times from accurate mass extracted ion chromatograms for plasma or feces samples.
[c]For c-eluting components, % ROI refers to the total contribution of all components.

The chemical structures of metabolite KD025m1 and previously unidentified metabolites of belumosudil discovered in this Study can be illustrated as follows:

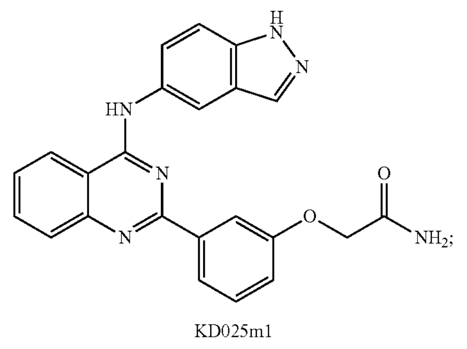

KD025m1

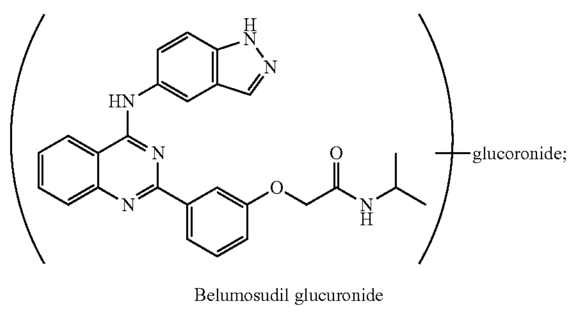

Belumosudil glucuronide

-continued

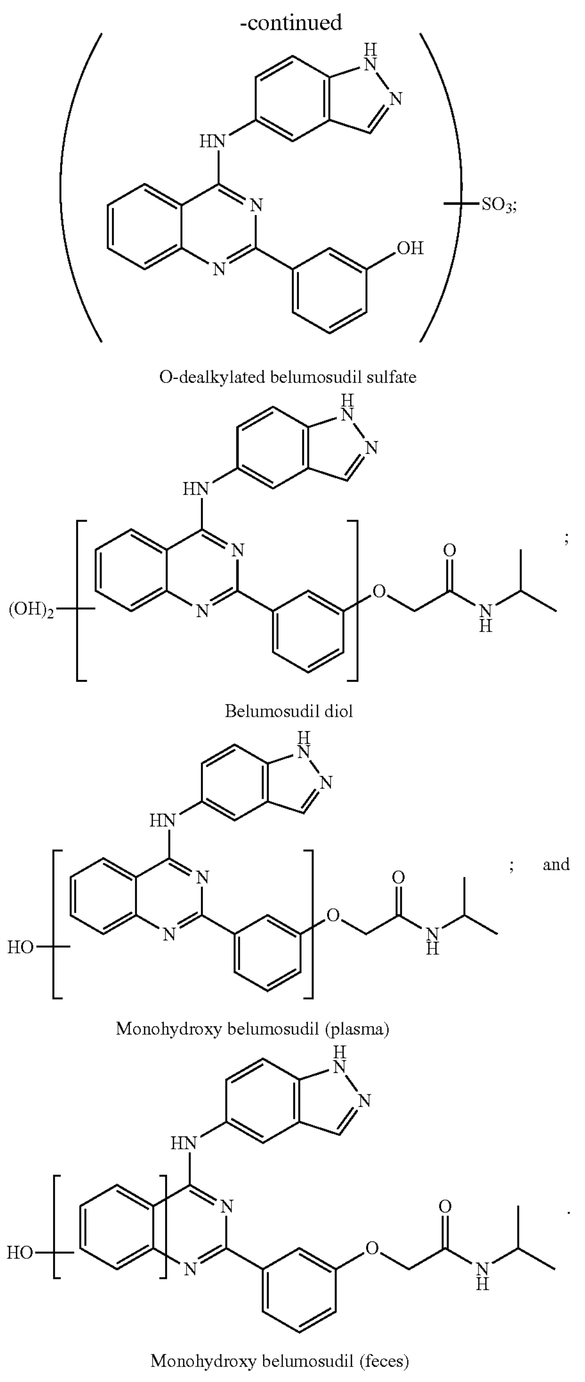

O-dealkylated belumosudil sulfate

;

Belumosudil diol

; and

Monohydroxy belumosudil (plasma)

.

Monohydroxy belumosudil (feces)

Overall, the belumosudil safety profile was as expected when administered to healthy subjects both as a 200-mg tablet followed by a [$^{14}$C]-belumosudil microtracer infusion (part 1) and as a 200-mg [$^{14}$C]belumosudil capsule (part 2). There were no deaths, serious AEs, AEs of severe intensity, or AEs leading to subject withdrawal during either part of this study. One treatment-emergent AE was recorded in part 1 (mild, possibly related rash), and no treatment-emergent AEs were reported in part 2. The event resolved spontaneously 2.5 hours after onset. No clinically significant laboratory, vital sign, electrocardiogram, or physical examination findings were reported following dosing in either part of the study.

This study evaluated the absorption, metabolism, and excretion properties of belumosudil in humans following oral doses of unlabeled tablets and radiolabeled capsules, as well as an IV microtracer of radiolabeled belumosudil in healthy male subjects. As described in the Methods section, a microtracer approach was taken to accurately characterize the IV PK profile without encountering dose-dependent kinetics or conducting additional toxicology studies with the IV formulation. Use of the highly sensitive AMS method permitted maximum data acquisition by allowing precise measurement of [$^{14}$C]-belumosudil while quantification of unlabeled belumosudil occurred by standard HPLC-MS/MS. A [$^{14}$C] label was selected because it could be easily introduced in a metabolically stable position in the backbone of belumosudil, thereby ensuring adequate mass balance determination and metabolite profiling. The synthesis and isolation of [$^{14}$C]-belumosudil relied on chemical processes identical to those used in the production of belumosudil.

In part 1, absolute bioavailability based on dose-adjusted $AUC_{inf,oral}/AUC_{inf,IV}$ was estimated to be 63.7% after oral administration of the marketed 200-mg belumosudil tablet. Following IV infusion of 100 μg [$^{14}$C]-belumosudil, the total clearance after IV administration was lower than typical hepatic blood flow rates, indicating a low extraction ratio (≈0.3). Apparent volume of distribution was higher than total body water, demonstrating distribution of [$^{14}$C]-belumosudil into tissue. Half-life values following IV and oral dosing were comparable at ≈5 to 6 hours and are similar to values observed in earlier clinical trials.

Following administration of a 200-mg [$^{14}$C]-belumosudil capsule in part 2, the majority of total radioactivity was recovered in feces (85%) and <5% was recovered in urine, suggesting minimal renal elimination of belumosudil. Based on an absolute bioavailability of 63.7% in part 1 and the low recovery of radioactivity in urine, the predominant route of clearance of [$^{14}$C]-belumosudil and associated metabolites is likely biliary and/or intestinal. Total radioactivity whole blood:plasma ratios ranged from 0.53 to 1.16, indicating little to no preferential distribution of total radioactivity into the cellular components of whole blood.

The concentrations of belumosudil, KD025m2, and KD025m1 present in total circulating radioactivity in plasma in part 2 suggested the potential for other circulating metabolites to be present in plasma. In addition, half-life for total radioactivity was longer than that of belumosudil (geometric means, 18.0 and 5.3 hours, respectively), further supported the presence of other metabolites with longer elimination phases. Indeed, metabolites glucuronide and sulfate derivative, in addition to belumosudil diol, were identified for the first time in humans through this study using standard LC-MS/MS metabolite profiling techniques. The human metabolic pathway for belumosudil was developed through this study and is presented in FIG. 3.

In addition to parent, major metabolite KD025m2, and active minor metabolite KD025m1, other metabolites were identified in plasma as O-dealkylated belumosudil sulfate and belumosudil glucuronide. In feces, parent, KD025m2, O-dealkylated belumosudil sulfate, monohydroxy-belumosudil, and belumosudil diol were identified as metabolites accounting for >10% of the radioactive dose. No metabolites in urine were found to account for >10% of the dose.

Example 2: In Vitro Studies and Inhibition of ROCK1 and ROCK2 Enzymatic Activity by Belumosudil and Metabolites The effects of belumosudil and main metabolites, KD025m1 and KD025m2, in inhibiting ROCK2 enzymatic activity were evaluated in enzymes purified from cell supernatants or tissue homogenates.

Full length rat ROCK1 and ROCK2 proteins were isolated from various tumor cell lines or tissues by immunoabsorption to 24-well microtiter plates pre-coated with antibodies specific for each isozyme. Reactions were initiated by the addition of S6 kinase substrate peptide, [γ33P]ATP, and study drug, and incubated at 37° C. for 20 minutes. Reactions were terminated by addition of phosphoric acid and the radioactivity was quantified using standard methods.

The results show that belumosudil inhibited ROCK2 enzymatic activity with approximately 30-fold greater inhibition compared to ROCK1; i.e. an $IC_{50}$ more than 30-fold lower than its inhibitory effect on ROCK1.

Results further showed inhibition activity of belumosudil metabolites. Table 4 shows the order of the inhibitory effect of belumosudil (KD025), KD025m1, and KD025m2 on ROCK enzymes. Fasudil and Y-27362 are included as reference ROCK inhibitors. The metabolite KD025m1 inhibited ROCK2 with a comparable Ki value to belumosudil, while inhibition of ROCK2 by the second metabolite KD025m2 was approximately 6-fold lower.

TABLE 4

ROCK 2 Inhibition by Belumosudil and Metabolites KD025m1 and KD025m2

| | Ki (nM) | | | | |
|---|---|---|---|---|---|
| Enzyme | KD025 | KD025m1 | KD025m2 | Y-27362 | Fasudil |
| ROCK2 | 40 ± 5 | 55 ± 2 | 338 ± 55 | 45 ± 5 | 55 ± 5 |

Although the present invention has been described in some detail by way of illustration and example for purposes of clarity and understanding, the descriptions and examples should not be construed as limiting the scope of the invention. The disclosures of all patent and scientific literature cited herein are expressly incorporated herein in their entirety by reference.

The invention claimed is:

1. An isolated or synthesized monohydroxy belumosudil or belumosudil diol, or a pharmaceutically acceptable salt thereof.

2. A pharmaceutical composition comprising a compound according to claim 1, and a pharmaceutically acceptable carrier.

* * * * *